(12) United States Patent
Rabinow et al.

(10) Patent No.: US 9,084,763 B2
(45) Date of Patent: Jul. 21, 2015

(54) METHODS FOR TREATING TACHYCARDIA AND/OR CONTROLLING HEART RATE WHILE MINIMIZING AND/OR CONTROLLING HYPOTENSION

(71) Applicants: BAXTER INTERNATIONAL INC., Deerfield, IL (US); BAXTER HEALTHCARE SA, Glattpark (Opifkon) (CH)

(72) Inventors: Barrett Rabinow, Skokie, IL (US); Jeff McKee, McHenry, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 0 days.

(21) Appl. No.: 14/075,857

(22) Filed: Nov. 8, 2013

(65) Prior Publication Data

US 2014/0066503 A1    Mar. 6, 2014

Related U.S. Application Data

(62) Division of application No. 13/359,065, filed on Jan. 26, 2012, now Pat. No. 8,686,036.

(60) Provisional application No. 61/436,992, filed on Jan. 27, 2011.

(51) Int. Cl.
*A61K 31/34* (2006.01)
*A61K 31/216* (2006.01)
*A61K 31/24* (2006.01)

(52) U.S. Cl.
CPC .............. *A61K 31/216* (2013.01); *A61K 31/24* (2013.01)

(58) Field of Classification Search
CPC .................................................. A61K 31/24
USPC .................................. 514/534, 533, 538, 821
See application file for complete search history.

(56) References Cited

U.S. PATENT DOCUMENTS

| | | | |
|---|---|---|---|
| 4,857,552 A | 8/1989 | Rosenberg et al. | |
| 5,017,609 A | 5/1991 | Escobar et al. | |
| 5,849,843 A | 12/1998 | Laurin et al. | |
| 5,977,409 A | 11/1999 | Erhardt | |
| 5,998,019 A | 12/1999 | Rosenbaum et al. | |
| 6,310,094 B1 | 10/2001 | Liu et al. | |
| 8,829,047 B2* | 9/2014 | Gass et al. | 514/534 |
| 2012/0277309 A1 | 11/2012 | Gass et al. | |

FOREIGN PATENT DOCUMENTS

| | | |
|---|---|---|
| CN | 101323580 A | 12/2008 |
| CN | 101881755 A | 11/2010 |
| CN | 101891636 A | 11/2010 |
| CN | 102106846 A | 6/2011 |
| WO | WO-85/04580 A1 | 10/1985 |
| WO | WO-87/03583 A1 | 6/1987 |
| WO | WO-88/01614 A1 | 3/1988 |
| WO | WO-89/11855 A1 | 12/1989 |
| WO | WO-02/076446 A1 | 10/2002 |
| WO | WO-2005/014042 A1 | 2/2005 |
| WO | WO-2008/153582 A1 | 12/2008 |

OTHER PUBLICATIONS

Anargan et al., Esmolol hydrochloride: an ultrashort-acting, β-adrenergic blocking agent, Clin. Pharm., 5:288-303 (1986).
Benvenuto et al., Morbidity and mortality of orthostatic hypotension: implications for management of cardiovascular disease, Am. J. Hypertens., 24(2):135-44 (2011).
Byrd et al., Safety and efficacy of esmolol (ASL-8052: an ultrashort-acting beta-adrenergic blocking agent) for control of ventricular rate in supraventricular tachycardias, J. Am. Coll. Cardiol., 3(2Pt. 1):394-9 (1984).
Conolly et al., Metabolism of isoprenaline in dog and man, Br. J. Pharmacol., 46(3):458-72 (1972).
Deegan et al., β-Receptor antagonism does not fully explain esmolol-induced hypotension, Clin. Pharmacol. Ther., 56:223-8 (1994).
DeStefano et al., Autosomal dominant orthostatic hypotensive disorder maps to chromosome 18q, Am. J. Hum. Genet., 63(5):1425-30 (1998).
Esmolol Hydrocholride Injection Ready-to-Use 10 mL Vials, Packaging Insert, Baxter Healthcare Corporation (Mar. 2003).
Fleischer, 2009 ACCF/AHA focused update on perioperative beta blockade incorporated into teh ACC/AHA 2007 guidelines on perioperative cardiovascular evaluation and care for noncardiac surgery, J. Am. Coll. Cardiol., 54:e13-e118 (2009).
Hartmann et al., The incidence and risk factors for hypotension after spinal anesthesia induction: an analysis with automated data collection, Anesth. Analg., 94(6):1521-9 (2002).
Hessov et al., Experimental infusion thrombophlebitis. Importance of the pH of glucose solutions, Eur. J. Intensive Care Med., 2(2):97-101 (1976).
Hoover et al., Comparison of in vitro and in vivo models to assess venous irritation of parenteral antibiotics, Fundam. Appl. Toxicol., 14(3):589-97 (1990).
International Preliminary Report on Patentability, PCT/US2012/022696, Apr. 30, 2013.
International Search Report and Written Opinion from corresponding international application No. PCT/US2012/022696, mailing date Apr. 5, 2012.
Jacobs et al., Esmolol and left ventricular function in the awake dog, Anesthesiology, 68(3):373-8 (1988).
Johnson et al., Development of an in vivo model for assessment of drug-induced vascular injury, J. Oral Maxillofac. Surg., 47(8):819-22 (1989).

(Continued)

*Primary Examiner* — Kevin E Weddington
(74) *Attorney, Agent, or Firm* — Marshall, Gerstein & Borun LLP

(57) ABSTRACT

A method of treating tachycardia while minimizing and/or controlling hypotension associated with such treatment includes administering a therapeutically effective amount of a pharmaceutical composition comprising the S-isomer of esmolol to a subject in need thereof.

17 Claims, 13 Drawing Sheets

(56) References Cited

OTHER PUBLICATIONS

Ko et al., A new dosing regimen for esmolol to treat supraventricular tachyarrhythmia in Chinese patients, J. Am. Coll. Cardiol., 23(2):302-6 (1994).

Laupland, Population-based epidemiology of intensive care: critical importance of ascertainment of residency status, Critical Care, 8:R431-6 (2004).

Mehvar et al., Stereospecific pharmacokinetics and pharmacodynamics of beta-adrenergic blockers in humans, J. Pharm. Pharm. Sci., 4(2):185-200 (2001).

Moreno et al., Intrapericardial beta-adrenergic blockade with esmolol exerts a potent antitachycardic effect without depressing contractility, J. Cardiovasc. Pharmacol., 36(6):722-7 (2000).

Murthy et al., Cardiovascular pharmacology of ASL-8052, an ultra-short acting beta blocker, Eur. J. Pharmacol., 92(1-2):43-51 (1983).

NDA 19-386: Review and Evaluation of Pharmacology and Toxicology Data, American Critical Care, McGraw Park, Illinois (1986).

Ornstein et al., Are all effects of esmolol equally rapid in onset?, Anesth. Analg. 81:297-300 (1995).

Quon et al., Pharmacodynamics and onset of action of esmolol in anesthetized dogs, J. Pharmacol. Exp. Ther., 237(3):912-8 (1986).

Reich et al., Predictors of hypotension after induction of general anesthesia, Anesth. Analg., 101(3):622-8 (2005).

Reilly et al., Ultra-short-acting beta-blockade: a comparison with conventional beta-blockade, Clin. Pharmacol. Ther., 38(5):579-85 (1985).

Robertson, Genetics and molecular biology of hypotension, Curr. Opin. Nephrol. Hypertens., 3(1):13-24 (1994).

Shaffer et al., Beta-adrenoreceptor antagonist potency and pharmacodynamics of ASL-8123, the primary acid metabolite of esmolol, J. Cardiovasc. Pharmacol., 11(2):187-92 (1988).

Sung et al., Clinical experience with esmolol, a short-acting beta-adrenergic blocker in cardiac arrhythmias and myocardial ischemia, J. Clin. Pharmacol., 26 (suppl A): A15-A26 (1986).

Tang et al., Stereoselective RP-HPLC determination of esmolol enantiomers in human plasma after pre-column derivatization, J. Biochem. Biophys. Methods, 59(2):159-66 (2004).

Wu et al., Population-based study on the prevalence and risk factors of orthostatic hypotension in subjects with pre-diabetes and diabetes, Diabetes Care, 32(1):69-74 (2009).

Yu et al., The safety of perioperative esmolol: a systematic review and meta-analysis of randomized controlled trials, Anesth. Analg., 112(2):267-81 (2011).

Zaugg et al., Adrenergic receptor genotype but not perioperative bisoprolol therapy may determine cardiovascular outcome in at-risk patients undergoing surgery with spinal block: the Swiss Beta Blocker in Spinal Anesthesia (BBSA) study: a double-blinded, placebo-controlled, multicenter trial with 1-year follow-up, Anesthesiology, 107(1):33-44 (2007).

Zaugg et al., Genetic modulation of adrenergic activity in the heart and vasculature: Implications for perioperative medicine, Anesthesiology, 102:429-46 (2005).

\* cited by examiner

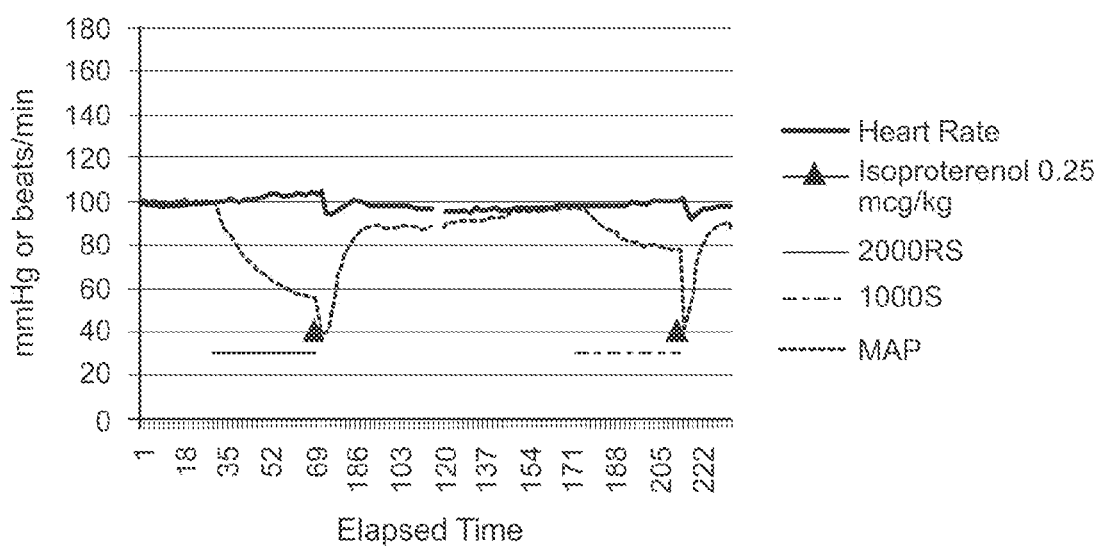

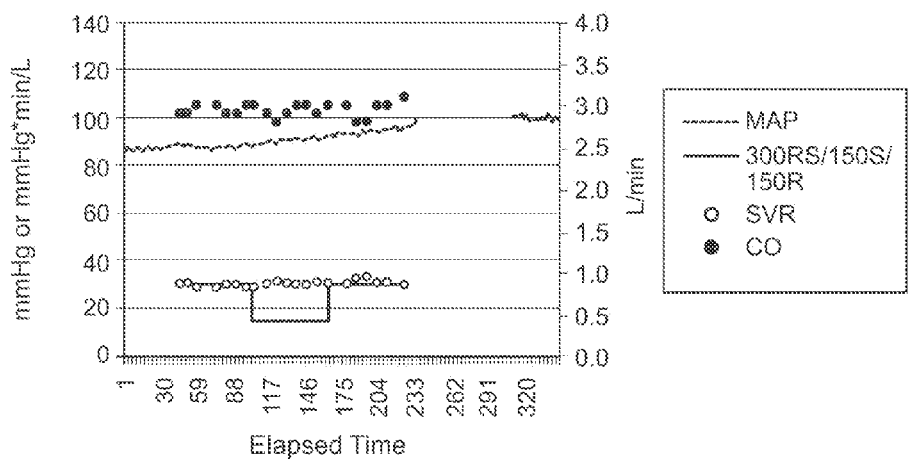
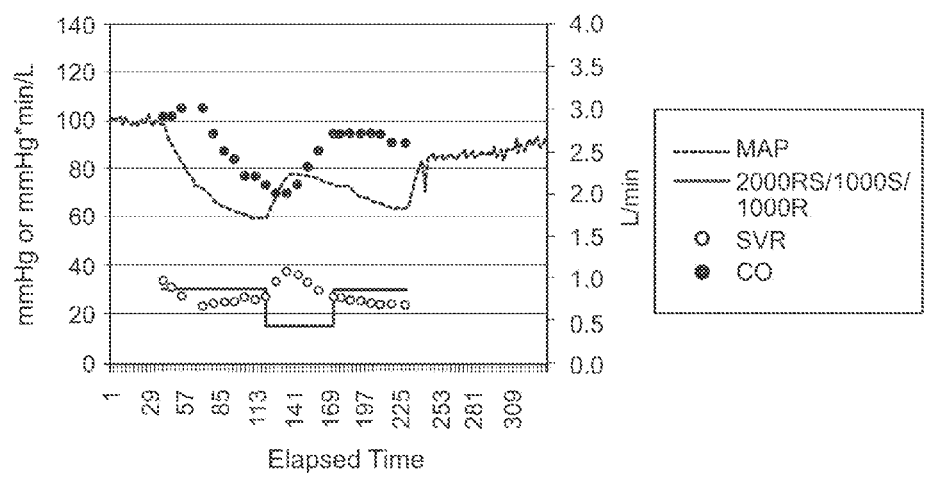

METHODS FOR TREATING TACHYCARDIA AND/OR CONTROLLING HEART RATE WHILE MINIMIZING AND/OR CONTROLLING HYPOTENSION

FIELD OF THE INVENTION

The invention relates to methods of treating tachycardia and/or of controlling heart rate while minimizing and/or controlling hypotension associated therewith, the method comprising administering a therapeutically effective amount of a pharmaceutical composition comprising the S-isomer of esmolol.

BACKGROUND

Esmolol hydrochloride (methyl-3-[4-(2-hydroxy-3-isopropylamino) propoxy]phenylpropionate hydrochloride) is a 50:50 racemic mixture of S- and R-isomers. Esmolol hydrochloride is a fast-acting beta-blocker used for treatment of cardiac disorders such as tachycardia, including supraventricular tachycardia, intraoperative tachycardia and postoperative tachycardia, and hypertension. Most currently available beta-blockers have relatively long onset times. However, it is often desirable in the critical care setting to quickly reduce rate and/or improve rhythmicity during a cardiac crisis, e.g., during or shortly after a myocardial infarction. Conventional beta-blocking agents can be employed for such treatment, but their relatively long onset times can prevent a clinician from effectively titrating the dose quickly, e.g., when a patient is in crisis. Because of esmolol hydrochloride's relatively fast onset time, feedback is immediate and, thus, dosing can be advantageously adjusted quickly according to the patient's response.

Esmolol hydrochloride differs from conventional beta-blocking compounds in that it contains an ester functional group which can be rapidly hydrolyzed. Esmolol hydrochloride has a short duration in vivo due to the presence of the ester group and is indicated for the rapid control of ventricular rate in patients with supraventricular tachycardia (i.e., atrial fibrillation or atrial flutter) in perioperative, postoperative, or other emergent circumstances where short term control of ventricular rate with a short-acting agent is desirable. Esmolol hydrochloride is also indicated for the treatment of tachycardia and hypertension that occur during induction and tracheal intubation, during surgery, on emergence from anesthesia, and in the postoperative period. Esmolol hydrochloride is typically administered by infusion.

A shortcoming of esmolol hydrochloride involves the development of hypotension in a significant number of patients to whom it is administered. Hypotension is listed on the packaging insert as a commonly occurring adverse event associated with esmolol treatment. See Esmolol Hydrochloride Injection Ready-to-use 10 mL Vials, packaging insert (Baxter Healthcare Corporation); see also Byrd et al., *JACC*, 3:394-9 (1984). In fact, 20-50% of patients treated with esmolol hydrochloride experienced hypotension in clinical trials. See Esmolol Hydrochloride Injection Ready-to-use 10 mL Vials, packaging insert. Hypotension can occur at any dose but is dose-related so that esmolol hydrochloride doses greater than 200 μg/kg/min are generally not recommended. Id. Hypotension can cause oxygen deprivation in the brain and vital organs, ultimately resulting in shock. Hypotension can also cause dizziness and fainting. Currently, hypotension is generally controlled in patients to whom esmolol is administered by carefully titrating the infusion rate of the drug. It is particularly important to closely monitor patients whose pretreatment blood pressure is low. A desired higher infusion rate often cannot be used to lower the heart rate of a patient in stress because of concern that hypotension may develop and/or because of the actual development of hypotension. As a result, esmolol hydrochloride administration often takes longer to achieve its desired therapeutic effect than it otherwise would by utilizing the desired higher infusion rate.

In view of the foregoing, it would be advantageous to retain the efficacious beta-blockade effects of esmolol hydrochloride while minimizing the bothersome hypotension that occurs with significant frequency in esmolol hydrochloride administration.

SUMMARY OF THE INVENTION

The present disclosure provides methods of treating cardiac conditions (e.g., tachycardia and hypertension) and/or of controlling heart rate by administering pharmaceutical compositions comprising the S-isomer of esmolol in order to minimize the hypotension often associated with administration of the racemic mixture of esmolol hydrochloride.

In one aspect, the invention provides a method for treating tachycardia in a subject, the method comprising administering to the subject a therapeutically effective amount of a pharmaceutical composition comprising (S)-methyl-3-[4-(2-hydroxy-3-isopropylamino) propoxy]phenylpropionate or pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt thereof, and the subject is in need of treatment for tachycardia with control of associated hypotension.

In another aspect, the invention provides a method for treating tachycardia in a subject in need thereof, the method comprising administering to the subject a therapeutically effective amount of a pharmaceutical composition comprising (S)-methyl-3-[4-(2-hydroxy-3-isopropylamino) propoxy]phenylpropionate or a pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt, and wherein the therapeutically effective amount is administered at a hypotension controlling amount.

In another aspect, the invention provides a method for controlling heart rate in a subject, the method comprising administering to the subject a therapeutically effective amount of a pharmaceutical composition comprising (S)-methyl-3-[4-(2-hydroxy-3-isopropylamino) propoxy]phenylpropionate or pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt thereof, and the subject is in need of heart rate control with control of associated hypotension.

In another aspect, the invention provides a method for controlling heart rate in a subject in need thereof, the method comprising administering to the subject a therapeutically effective amount of a pharmaceutical composition comprising (S)-methyl-3-[4-(2-hydroxy-3-isopropylamino) propoxy]phenylpropionate or a pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt, and wherein the therapeutically effective amount is administered at a hypotension controlling amount.

Other features and advantages of the present invention will become apparent from the following detailed description and claims.

BRIEF DESCRIPTION OF THE DRAWINGS

FIGS. 6A-6C illustrate the results of experiments to evaluate whether the attenuated hypotension observed with the S-isomer formulations of FIGS. 2-5 reduced the efficacy (i.e., ability to control isoproterenol-induced tachycardia) of the S-isomer formulations as compared with the racemic formulations.

FIGS. 7A and 7B illustrate the results of experiments to evaluate the effects of administering pharmaceutical compositions comprising racemic mixtures of esmolol as compared to pharmaceutical compositions comprising the R-isomer of esmolol and pharmaceutical compositions comprising the S-isomer of esmolol.

DETAILED DESCRIPTION OF THE INVENTION

Figure 1:
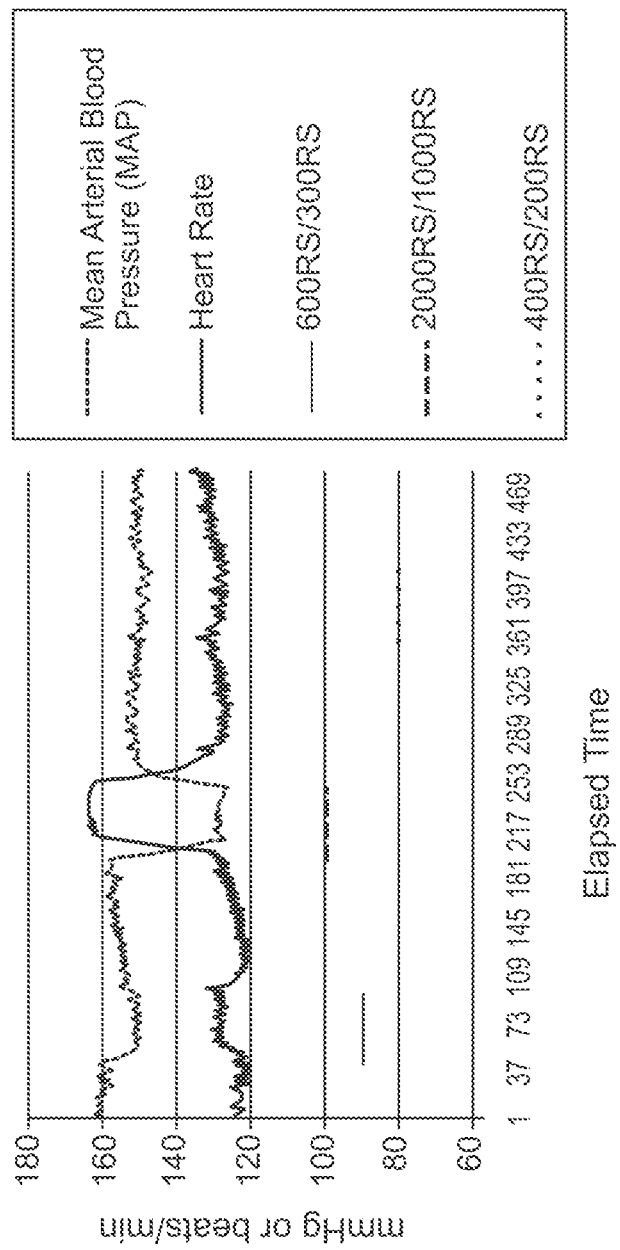
FIG. 1 illustrates an animal model for predicting the potential hypotensive response associated with esmolol hydrochloride injection in human patients.
Figure 2A:
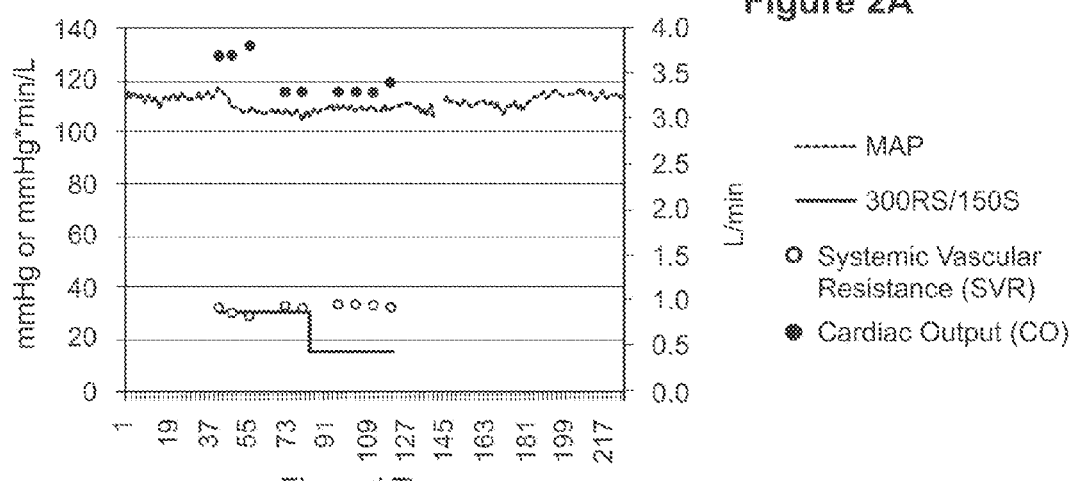
FIGS. 2A-2C illustrate the results of experiments to evaluate the effects of administering pharmaceutical compositions comprising racemic mixtures of esmolol as compared to pharmaceutical compositions comprising the S-isomer of esmolol. "RS" indicates the racemic mixture of esmolol and "S" indicates the S-isomer of esmolol.
Figure 2B:
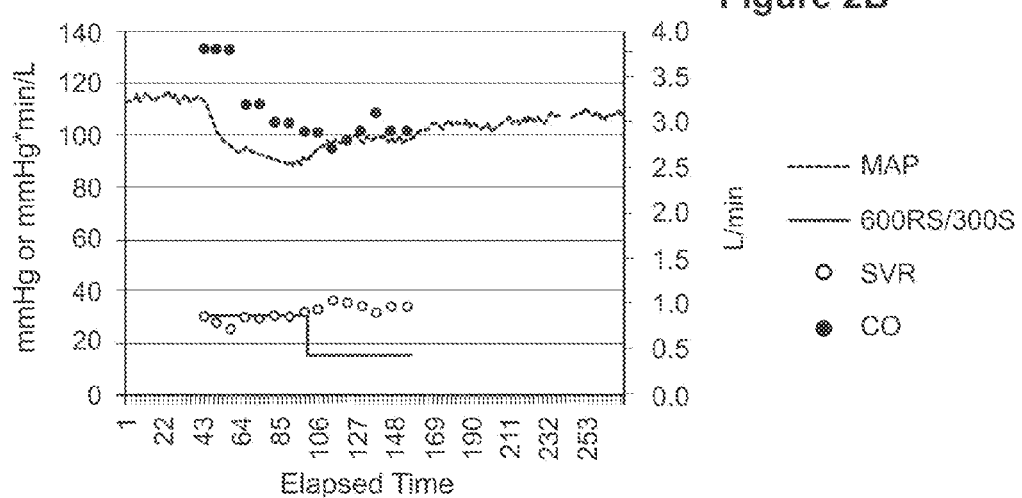
Figure 2C:
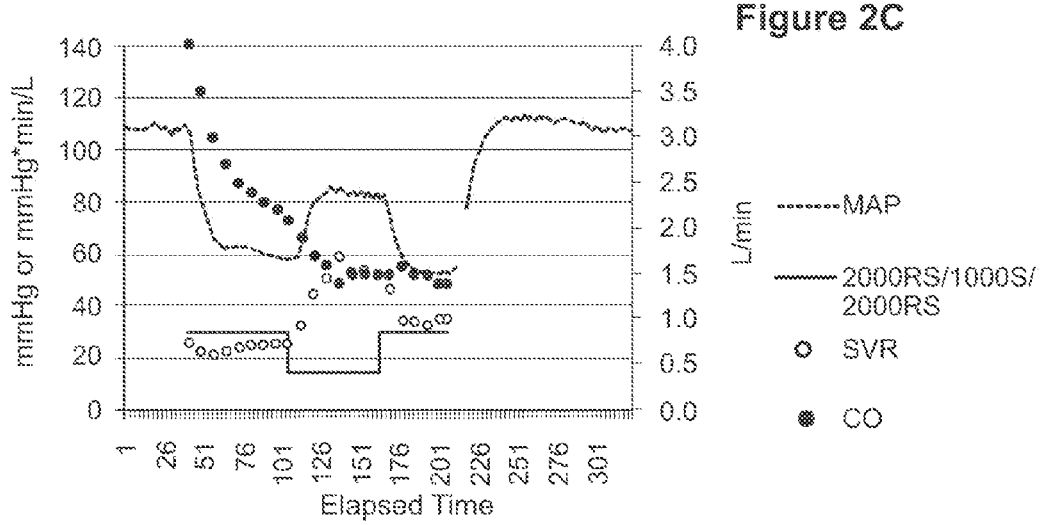

The invention disclosed herein provides improved methods of treating cardiac conditions (e.g., tachycardia and hypertension) and/or of controlling heart rate while concurrently minimizing and/or controlling hypotension often associated with the administration of pharmaceutical compositions comprising the racemic mixture of esmolol by administering pharmaceutical compositions comprising the S-isomer of esmolol. The present inventors unexpectedly and surprisingly found that administering a therapeutically effective amount of a pharmaceutical composition comprising the S-isomer of esmolol, and preferably the S-isomer of esmolol hydrochloride, demonstrates substantially similar heart rate control and causes significantly less hypotension than administration of the racemic mixture, particularly relative to administration of an amount of the racemic mixture that corresponds to an equitherapeutic amount of the S-isomer of esmolol. As a result of the reduced tendency to induce hypotension, therapeutic drug concentrations or infusion rates of the S-isomer of esmolol may be administered more safely than with the racemic mixture. Moreover, patients susceptible to hypotension with the esmolol racemic mixture may be treated with the S-isomer of esmolol while minimizing and/or controlling hypotension. Therefore, the present invention advantageously affords a significantly higher degree of safety by beneficially minimizing and/or controlling the development of hypotension in patients who receive compositions comprising the S-isomer of esmolol, while also advantageously allowing higher therapeutic doses of the S-isomer of esmolol to be utilized than in prior art methods in which compositions comprising the racemic mixture were administered. Thus, the invention allows the clinician to advantageously attend to the tachycardia and/or hypertension experienced by the patient or to more easily control the heart rate of the patient while minimizing the need for careful titration of the drug and for closely monitoring patients whose pretreatment blood pressure is low.

In one aspect, the invention provides a method for treating tachycardia in a subject, the method comprising administering to the subject a therapeutically effective amount of a pharmaceutical composition comprising (S)-methyl-3-[4-(2-hydroxy-3-isopropylamino) propoxy]phenylpropionate or pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt thereof, and the subject is in need of treatment for tachycardia with control of associated hypotension.

In another aspect, the invention provides a method for treating tachycardia in a subject in need thereof, the method comprising administering to the subject a therapeutically effective amount of a pharmaceutical composition comprising (S)-methyl-3-[4-(2-hydroxy-3-isopropylamino) propoxy]phenylpropionate or a pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt, and wherein the therapeutically effective amount is administered at a hypotension controlling amount.

In an additional aspect, the invention provides a method for controlling heart rate in a subject, the method comprising administering to the subject a therapeutically effective amount of a pharmaceutical composition comprising (S)-methyl-3-[4-(2-hydroxy-3-isopropylamino) propoxy]phenylpropionate or pharmaceutically acceptable salt thereof, wherein the pharmaceutical composition is substantially free of (R)-methyl-3-[4-(2-hydroxy-3-isopropylamino) propoxy] phenylpropionate or a pharmaceutically acceptable salt thereof, and the subject is in need of heart rate control with control of associated hypotension.

In yet another aspect, the invention provides a method for controlling heart rate in a subject in need thereof, the method comprising administering to the subject a therapeutically effective amount of a pharmaceutical composition comprising (S)-methyl-3-[4-(2-hydroxy-3-isopropylamino) propoxy]phenylpropionate or a pharmaceutically acceptable salt thereof, wherein the pharmaceutical composition is substantially free of (R)-methyl-3-[4-(2-hydroxy-3-isopropylamino) propoxy]phenylpropionate or a pharmaceutically acceptable salt, and wherein the therapeutically effective amount is administered at a hypotension controlling amount.

The cardiac conditions and/or disorders which can be treated by the methods of the invention include any cardiac condition known to benefit from treatment with esmolol. Such cardiac conditions include, but are not limited to, tachycardia (e.g., supraventricular tachycardia, intraoperative and postoperative tachycardia) and hypertension (e.g., intraoperative and postoperative hypertension). Moreover, the methods of the invention can also be used to control heart rate in a patient, when clinically desirable, whether or not the subject has one of the aforementioned cardiac conditions.

As used herein, the terms "pharmaceutical composition comprising (S)-methyl-3-[4-(2-hydroxy-3-isopropylamino) propoxy]phenylpropionate or a pharmaceutically acceptable salt thereof," and "pharmaceutical composition comprising the S-isomer of esmolol" refer to pharmaceutical compositions which are substantially free of (R)-methyl-3-[4-(2-hydroxy-3-isopropylamino) propoxy]phenylpropionate or a pharmaceutically acceptable salt thereof. The term "substantially free of (R)-methyl-3-[4-(2-hydroxy-3-isopropylamino) propoxy]phenylpropionate" refers to compositions that contain less than 10% by weight, less than 5% by weight, less than 3% by weight, less than 2% by weight, less than 1% by weight, and/or less than 0.5% by weight (R)-methyl-3-[4-(2-hydroxy-3-isopropylamino) propoxy]phenylpropionate or a pharmaceutically acceptable salt thereof based on the total amount of methyl-3-[4-(2-hydroxy-3-isopropylamino) propoxy]phenylpropionate or pharmaceutically acceptable salt thereof in the composition. Preferably, compositions "substantially free of (R)-methyl-3-[4-(2-hydroxy-3-isopropylamino) propoxy]phenylpropionate" contain 5 wt. % or less of (R)-methyl-3-[4-(2-hydroxy-3-isopropylamino) propoxy] phenylpropionate or a pharmaceutically acceptable salt thereof based on the total amount of methyl-3-[4-(2-hydroxy-3-isopropylamino) propoxy]phenylpropionate or pharmaceutically acceptable salt thereof in the composition, e.g., less than 3 wt. %, less than 2 wt. %, less than 1 wt. %, and/or less than 0.5 wt. %. The total esmolol content can be determined using a standard HPLC column or similar analytical method known in the art. The respective relative contents of the S-isomer of esmolol and the R-isomer of esmolol in a given composition can be determined using a chiral HPLC method or similar analytical method known in the art. See, e.g., Tang et al., *J. Biochem. Biophys. Methods*, 59:159-166 (2004).

In one aspect, a "therapeutically effective amount" refers to an amount of a pharmaceutical composition comprising (S)-methyl-3-[4-(2-hydroxy-3-isopropylamino) propoxy]phenylpropionate or a pharmaceutically acceptable salt thereof which is sufficient to control tachycardia and/or hypertension. Thus, an amount sufficient to control tachycardia includes but is not limited to an amount sufficient to alleviate and/or ameliorate tachycardia and/or hypertension.

In another aspect, a "therapeutically effective amount" refers to an amount of a pharmaceutical composition comprising (S)-methyl-3-[4-(2-hydroxy-3-isopropylamino) propoxy]phenylpropionate or a pharmaceutically acceptable salt thereof which is sufficient to control heart rate. Thus, an amount sufficient to control heart rate includes but is not limited to an amount sufficient to control and/or reduce an elevated heart rate.

In all aspects of the disclosure, the therapeutically effective amount can be a hypotension controlling amount as defined below.

The term "hypotension controlling amount" refers to an amount of a pharmaceutical composition comprising (S)-methyl-3-[4-(2-hydroxy-3-isopropylamino) propoxy]phenylpropionate or a pharmaceutically acceptable salt thereof that provides the therapeutic benefits of a composition comprising the racemic mixture of esmolol (e.g., control of tachycardia and/or hypertension and/or control of heart rate) while minimizing the hypotension often associated with administration of the racemic mixture of esmolol. Therefore, a hypotension controlling amount can be any therapeutically effective amount which does not cause hypotension in a subject, particularly relative to administration of the racemic mixture which has been shown to induce hypotension in 20-50% of humans. See Esmolol Hydrochloride Injection Ready-to-use 10 mL Vials, packaging insert. Thus, in various aspects, a hypotension controlling amount is greater than or equal to 37.5 nmol/kg/min of the S-isomer of esmolol (i.e., about 12.5 µg/kg/min of the S-isomer of esmolol hydrochloride) which corresponds to about 25 µg/kg/min of the racemic mixture of esmolol hydrochloride, greater than or equal to 75 nmol/kg/min of the S-isomer of esmolol (e.g., about 25 µg/kg/min of the S-isomer of esmolol hydrochloride) which corresponds to about 50 µg/kg/min of the racemic mixture of esmolol hydrochloride, and/or greater than or equal to 0.15 µmol/kg/min of the S-isomer of esmolol (e.g., about 50 µg/kg/min of the S-isomer of esmolol hydrochloride) which corresponds to about 100 µg/kg/min of the racemic mixture of esmolol hydrochloride. Moreover, because doses of 200 µg/kg/min of racemic esmolol hydrochloride are generally not recommended (see Esmolol Hydrochloride packaging insert), in one aspect, a hypotension controlling amount of a pharmaceutical composition comprising the S-isomer of esmolol or a pharmaceutically acceptable salt thereof can refer to a dose of the S-isomer of esmolol which is greater than or equal to 0.3 µmol/kg/min (e.g., about 100 µg/kg/min of the S-isomer of esmolol hydrochloride) which corresponds to about 200 µg/kg/min of the racemic mixture of esmolol hydrochloride. Other exemplary hypotension controlling amounts of a pharmaceutical composition comprising the S-isomer of esmolol in accordance with this aspect include but are not limited to greater than or equal to 0.45 µmol/kg/min of the S-isomer of esmolol (e.g., about 150 µg/kg/min of the S-isomer of esmolol hydrochloride) which corresponds to about 300 µg/kg/min of the racemic mixture of esmolol hydrochloride, greater than or equal to 0.6 µmol/kg/min of the S-isomer of esmolol (e.g., about 200 µg/kg/min of the S-isomer of esmolol hydrochloride) which corresponds to about 400 µg/kg/min of the racemic mixture of esmolol hydrochloride, greater than or equal to 0.75 µmol/kg/min of the S-isomer of esmolol (e.g., about 250 µg/kg/min of the S-isomer of esmolol hydrochloride) which corresponds to about 500 µg/kg/min of the racemic mixture of esmolol hydrochloride, greater than or equal to 0.90 µmol/kg/min of the S-isomer of esmolol (e.g., about 300 µg/kg/min of the S-isomer of esmolol hydrochloride) which corresponds to about 600 µg/kg/min of the racemic mixture of esmolol hydrochloride, greater than or equal to 1.05 µmol/kg/min of the S-isomer of esmolol (e.g., about 350 µg/kg/min of the S-isomer of esmolol hydrochloride) which corresponds to about 700 µg/kg/min of the racemic mixture of esmolol hydrochloride, greater than or equal to 1.125 µmol/kg/min of the S-isomer of esmolol (e.g., about 375 µg/kg/min of the S-isomer of esmolol hydrochloride) which corresponds to about 750 µg/kg/min of the racemic mixture of esmolol hydrochloride, greater than or equal to 1.20 µmol/kg/min of the S-isomer of esmolol (e.g., about 400 µg/kg/min of the S-isomer of esmolol hydrochloride) which corresponds to about 800 µg/kg/min of the racemic mixture of esmolol hydrochloride, greater than or equal to 1.35 µmol/kg/min of the S-isomer of esmolol (e.g., about 450 µg/kg/min of the S-isomer of esmolol hydrochloride) which corresponds to about 900 µg/kg/min of the racemic mixture of esmolol hydrochloride, greater than or equal to 1.5 µmol/kg/min of the S-isomer of esmolol (e.g., about 500 µg/kg/min of the S-isomer of esmolol hydrochloride) which corresponds to about 1000 µg/kg/min of the racemic mixture of esmolol hydrochloride, greater than or equal to 1.8 µmol/kg/min of the S-isomer of esmolol (e.g., about 600 µg/kg/min of the S-isomer of esmolol hydrochloride) which corresponds to about 1200 µg/kg/min of the racemic mixture of esmolol hydrochloride, greater than or equal to 2.1 µmol/kg/min of the S-isomer of esmolol (e.g., about 700 µg/kg/min of the S-isomer of esmolol hydrochloride) which corresponds to about 1400 µg/kg/min of the racemic mixture of esmolol hydrochloride, greater than or equal to 2.4 µmol/kg/min of the S-isomer of esmolol (e.g., about 800 µg/kg/min of a pharmaceutical composition comprising the S-isomer of esmolol hydrochloride) which corresponds to about 1600 µg/kg/min of the racemic mixture of esmolol hydrochloride, greater than or equal to 2.7 µmol/kg/min of the S-isomer of esmolol (e.g., about 900 µg/kg/min of the S-isomer of esmolol hydrochloride) which corresponds to about 1800 µg/kg/min of the racemic mixture of esmolol hydrochloride, and/or greater than or equal to 3.0 µmol/kg/min of the S-isomer of esmolol (e.g., about 1000 µg/kg/min of the S-isomer of esmolol hydrochloride) which corresponds to about 2000 µg/kg/min of the racemic mixture of esmolol hydrochloride. For example, a hypotension controlling amount of a pharmaceutical composition comprising the S-isomer or a pharmaceutically acceptable salt can be administered in an amount between 37.5 nmol/kg/min and 3.0 µmol/kg/min, between 37.5 nmol/kg/min and 1.5 µmol/kg/min, between 37.5 nmol/kg/min and 0.75 µmol/kg/min, between 75 nmol/kg/min and 3.0 µmol/kg/min, between 75 nmol/kg/min and 1.5 µmol/kg/min, between 75 nmol/kg/min and 0.75 µmol/kg/min, between 0.15 µmol/kg/min and 3.0 µmol/kg/min, between 0.15 µmol/kg/min and 1.5 µmol/kg/min, between 0.15 µmol/kg/min and 0.75 µmol/kg/min, between 0.3 µmol/kg/min and 1.5 µmol/kg/min, between 0.45 µmol/kg/min and 1.5 µmol/kg/min, between 0.6 µmol/kg/min and 1.5 µmol/kg/min, between 0.75 µmol/kg/min and 1.5 µmol/kg/min, between 0.90 µmol/kg/min and 1.5 µmol/kg/min, between 1.05 µmol/kg/min and 1.5 µmol/kg/min, and/or between 1.20 µmol/kg/min and 1.5 µmol/kg/min.

The term "pharmaceutically acceptable salt" refers to those salts which retain the biological efficacy and properties of the esmolol, and which are not biologically or otherwise undesirable. Such salts can be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In all disclosed embodiments, the pharmaceutically acceptable salt of (S)-methyl-3-[4-(2-hydroxy-3-isopropylamino) propoxy]phenylpropionate can be (S)-methyl-3-[4-(2-hydroxy-3-isopropylamino) propoxy]phenylpropionate hydrochloride.

In one aspect, the term a "subject in need thereof" (i.e., in need of tachycardia and/or hypertension treatment) is defined as an individual who would benefit from administration of a beta blocker to control tachycardia and/or hypertension.

In another aspect, the term a "subject in need thereof" (i.e., in need of heart rate control) is defined as an individual who would benefit from administration of a beta blocker to control an elevated heart rate.

The term "in need of treatment for tachycardia with control of associated hypotension" refers to an individual who would benefit from administration of a beta blocker to control tachycardia and/or hypertension and is susceptible to the development of associated hypotension at the administered dose.

The term "in need of heart rate control with control of associated hypotension" refers to an individual having an elevated heart rate who would benefit from administration of a beta blocker and is susceptible to the development of associated hypotension at the administered dose.

As used herein, the term "tachycardia" refers to an abnormally fast heart beat, typically for humans age 15 or older, a heart rate greater than 100 beats per minute at rest. "Supraventricular tachycardia" refers to such an abnormally fast heart beat originating in the atria.

As used herein, the term "hypotension" refers to abnormally low blood pressure. As appreciated by those of skill in the art, blood pressure characterized as "hypotensive" may vary from individual to individual. Hypotension, however, is generally defined as systolic pressure less than 90 mmHg and/or diastolic pressure less than 50 mmHg.

As used herein, the term "hypertension" refers to abnormally high blood pressure. As appreciated by those of skill in the art, blood pressure characterized as "hypertensive" may vary from individual to individual. Hypertension, however, is generally defined as systolic pressure greater than 140 mmHg and/or diastolic pressure greater than 90 mmHg.

As used herein, the term "elevated heart rate" refers to a heart rate that is more than 20 beats per minute higher than an individual's normal resting pulse, more typically more than 25 beats per minute higher than the individual's normal resting pulse, and/or more than 30 beats per minute higher than the individual's normal resting pulse. Such elevated heart rates may not be tachycardias as defined herein, but tachycardia are also encompassed by the foregoing definition of elevated heart rate.

While beta blockers are often manufactured and commercialized as the RS racemic mixture, the S-isomer is generally responsible for all of the beta blocking activity. See Mehvar and Brocks, *J. Pharm. Pharmaceut. Sci.*, 4(2):185-200 (2001). Consistent with the foregoing, the S-isomer of esmolol has been demonstrated to be about twice as potent as a beta-adrenergic-blocking agent than an equivalent amount of the racemic mixture. See International Patent Publication No. WO 88/01614. Thus, as used herein, the terms "equitherapeutic amount" or "therapeutically equivalent amount" refer to an amount of (S)-methyl-3-[4-(2-hydroxy-3-isopropylamino) propoxy]phenylpropionate or pharmaceutically acceptable salt thereof that provides the same therapeutic beta-blockade benefit as a given amount of the racemic mixture of methyl-3-[4-(2-hydroxy-3-isopropylamino) propoxy] phenylpropionate hydrochloride. In general, the equitherapeutic amount of (S)-methyl-3-[4-(2-hydroxy-3-isopropylamino) propoxy]phenylpropionate or pharmaceutically acceptable salt thereof is one-half the amount of the racemic mixture of methyl-3-[4-(2-hydroxy-3-isopropylamino) propoxy]phenylpropionate hydrochloride. In other words, if the racemic mixture is administered at a rate of 300 µg/kg/min, the equitherapeutic amount of the S-isomer of esmolol is 150 µg/kg/min.

The pharmaceutical composition of the present invention is suitable for parenteral administration to a patient. Suitable routes for parenteral administration include intravenous, subcutaneous, intradermal, intramuscular, intraarticular, and intrathecal. For example, the pharmaceutical composition comprising (S)-methyl-3-[4-(2-hydroxy-3-isopropylamino) propoxy]phenylpropionate or pharmaceutically acceptable salt thereof may be administered in the form of a bolus injection, intravenous infusion, or combination bolus injection/intravenous infusion. The ready-to-use formulation of the invention is preferably administered by intravenous infusion.

The pharmaceutical composition comprising (S)-methyl-3-[4-(2-hydroxy-3-isopropylamino) propoxy]phenylpropionate or pharmaceutically acceptable salt thereof typically takes the form of a sterile, ready-to-use composition that is suitable for infusion. The ready-to-use presentation avoids the inconvenience of diluting a concentrated small volume parenteral formulation into infusion diluents prior to infusion, as well as eliminates the risk of microbiological contamination during handling and dilution and any potential calculation or dilution error. As used herein, a "ready-to-use" formulation or composition is defined as a pharmaceutical composition comprising (S)-methyl-3-[4-(2-hydroxy-3-isopropylamino) propoxy]phenylpropionate or pharmaceutically acceptable salt thereof that does not need dilution before administration to the patient. Similarly, "suitable for parental infusion" refers to formulations or compositions wherein the pH and osmolarity have been adjusted to physiological or near-physiological levels appropriate for administration to the patient by infusion. Such formulations or compositions can be essentially free from propylene glycol and ethanol. In alternative embodiments, the pharmaceutical composition comprising the S-isomer of esmolol can also take the form of a concentrated formulation which must be diluted prior to administration.

When treating tachycardias, the administered dose of the pharmaceutical composition comprising the S-isomer of esmolol hydrochloride is typically titrated using the ventricular rate as a guide. Generally, the administered dose of the S-isomer of esmolol hydrochloride is between 12.5 µg/kg/minute and 1000 µg/kg/minute, between 12.5 µg/kg/minute and 500 µg/kg/minute, between 12.5 µg/kg/minute and 400 µg/kg/minute, between 12.5 µg/kg/minute and 300 µg/kg/minute, between 12.5 µg/kg/minute and 200 µg/kg/minute, and/or between 12.5 µg/kg/minute and 100 µg/kg/minute. For example, a representative dosing protocol for treating supraventricular tachycardia may include an initial loading dose of 250 µg S-isomer esmolol hydrochloride/kg body weight (µg/kg) infused over a minute duration followed by a maintenance infusion of 25 µg/kg/minute S-isomer of esmolol hydrochloride for 4 minutes to obtain a guide with respect to the responsiveness of ventricular rate. A lower initial maintenance dose of S-isomer of esmolol hydrochloride such as, for example, 12.5 µg/kg/minute, or a higher initial maintenance dose of S-isomer of esmolol hydrochloride such as, for example, 37.5 µg/kg/minute, 50 µg/kg/minute, 62.5 µg/kg/minute, 75 µg/kg/minute, 87.5 µg/kg/minute, or even 100 µg/kg/minute may be used. In the dose calculations for the compositions comprising the S-isomer of esmolol according to the invention, it is assumed that the administered esmolol comprises 100% S-isomer. In some instances, after the 4 minutes of initial maintenance infusion and depending on whether the desired ventricular response has been achieved, the loading dose of 250 µg/kg S-isomer of esmolol hydrochloride infused over a 1 minute period is repeated, followed by an additional maintenance infusion which may be continued at 25 µg/kg/minute or increased step-wise to 50 µg/kg/minute for 4 more minutes. If an adequate therapeutic effect is not observed at this point, a third loading dose of 250 µg/kg S-isomer of esmolol hydrochloride may be repeated over 1 minute and followed with an additional maintenance infusion of S-isomer of esmolol hydrochloride which may be continued at the original 25 µg/kg/minute or increased to either 50 µg/kg/minute or 75 µg/kg/minute for 4 minutes. Maintenance infusions may then be continued for up to 48 hours at up to 100 µg/kg/minute to achieve the desired therapeutic effect. After achieving an adequate control of the heart rate and a stable clinical status in patients with supraventricular tachycardia, transition to alternative antiarrhythmic agents such as propranolol, digoxin, or verapamil, may be accomplished. As will be appreciated by those of ordinary skill in the art, because the S-isomer of esmolol minimizes the hypotension often associated with administration of the racemic mixture of esmolol, the loading dose can be higher than 250 µg/kg S-isomer esmolol hydrochloride if higher doses are indicated because of the need to rapidly control severe tachycardias. Thus, the loading dose of the S-isomer of esmolol hydrochloride can be greater than or equal to 300 µg/kg/min, greater than or equal to 350 µg/kg/min, greater than or equal to 400 µg/kg/min, greater than or equal to 450 µg/kg/min, greater than or equal to 500 µg/kg/min, greater than or equal to 550 µg/kg/min, greater than or equal to 600 µg/kg/min, greater than or equal to 650 µg/kg/min, greater than or equal to 700 µg/kg/min, greater than or equal to 750 µg/kg/min, greater than or equal to 800 µg/kg/min, greater than or equal to 850 µg/kg/min, greater than or equal to 900 µg/kg/min, greater than or equal to 950 µg/kg/min, and/or greater than or equal to 1000 µg/kg/min. If a pharmaceutically acceptable salt of S-esmolol other than the hydrochloride salt is administered, the molar equivalent to the above ranges can be administered.

When immediate response/control is desired in a clinical situation, for example, when treating acute intraoperative tachycardia and/or acute intraoperative hypertension, a representative dosing protocol includes administering a bolus dose of approximately 500 µg/kg S-isomer of esmolol hydrochloride over 30 seconds, followed by infusion of 75 µg/kg/min S-isomer of esmolol hydrochloride, if necessary. The infusion rate can be adjusted up to 150 µg/kg/min S-isomer of esmolol hydrochloride to maintain (or achieve) to reach the desired heart rate and/or blood pressure, as necessary. Again, if a pharmaceutically acceptable salt of S-esmolol other than the hydrochloride salt is administered, the molar equivalent to the above ranges can be administered.

On the other hand, when gradual response/control is acceptable, for example, when treating postoperative tachycardia and/or postoperative hypertension, the representative dosing protocol for treating supraventricular tachycardia may be used. Additionally, the representative dosing protocol for treating supraventricular tachycardia may also be used by clinicians to successfully control the heart rates of patients having elevated heart rates (i.e., elevated relative to the patient's normal resting pulse, as previously described).

It will be appreciated that the treatment methods of the invention are useful in the fields of human medicine and veterinary medicine. Thus, the subject or individual to be treated may be an animal, for example, a mammal, preferably human.

Containers suitable for packaging the pharmaceutical composition comprising (S)-methyl-3-[4-(2-hydroxy-3-isopropylamino) propoxy]phenylpropionate or pharmaceutically acceptable salt thereof according to the present invention include numerous sealed containers known in the art including, but not limited to, vials, syringes, bags, bottles, and ampul presentations. Containers may be fabricated from glass or from polymeric materials. Ready-to-use formulations are typically packaged in vials, syringes, bags and bottles, while concentrated formulations are typically packaged in ampuls.

Pharmaceutical compositions according to the present invention can be prepared into small volume parenteral (SVP) and large volume parenteral (LVP) dosage forms. The dosage forms can be packaged in any suitable container. Suitable containers include, for example, glass vials, polymeric vials, ampuls, syringes, and bags with sizes ranging from 1 mL to 500 mL. SVP solutions are typically filled into ampules and vials in 1-100 mL presentations. In addition, syringes can be used as the container for a SVP, which are sold as "pre-filled syringes." The LVP presentations can be contained in bags or bottles. A preferred presentation for ready-to-use LVP is a polymeric bag.

Polymeric containers, such as polymeric bags, are preferably flexible and can contain or be free of polyvinylchloride (PVC). Preferred containers are free of PVC, such as those disclosed in U.S. Pat. Nos. 5,849,843 and 5,998,019. Polymeric containers can further be provided with a moisture barrier as a secondary packaging system to prevent the loss of water during storage and to further ensure the stability of the formulation. A preferred moisture barrier is an aluminum overpouch.

The pH of the pharmaceutical composition can affect the stability of the (S)-methyl-3-[4-(2-hydroxy-3-isopropylamino) propoxy]phenylpropionate or pharmaceutically acceptable salt thereof. The pH should be between 3.5 and 6.5, preferably between 4.5 and 5.5, more preferably about 5.0. The pH can be adjusted as known in the art, for example, by addition of sodium hydroxide or hydrochloric acid.

The S-isomer of esmolol or pharmaceutically acceptable salt thereof is typically present in the pharmaceutical composition according to the invention in a concentration ranging from 0.3 mM-3.0 M (i.e., corresponding to about 0.1-1000 mg/mL of S-isomer esmolol hydrochloride). Ready-to-use formulations generally contain 0.3 mM-300 mM (i.e., corresponding to about 0.1-100 mg/mL S-isomer esmolol hydrochloride), 3-150 mM (i.e., corresponding to about 1-50 mg/mL S-isomer esmolol hydrochloride), and/or 3-75 mM (i.e., corresponding to about 1-25 mg/mL S-isomer esmolol hydrochloride) of S-isomer esmolol or pharmaceutically acceptable salt thereof. Concentrated formulations may contain 300-1500 mM (i.e., corresponding to about 100-500 mg/mL S-isomer esmolol hydrochloride), for example, 300-750 mM (i.e., corresponding to about 100-250 mg/mL S-isomer esmolol hydrochloride) of S-isomer esmolol or pharmaceutically acceptable salt thereof.

Suitable buffering agents are known in the art, and are typically present in the pharmaceutical compositions according to the invention in a concentration ranging from 0.01-2 M. Ready-to-use formulations typically have buffering agent concentrations of 0.01-0.5 M, for example, 0.02-0.1 M. Concentrated formulations typically have buffering agent concentrations of 0.5-2 M. Exemplary buffering agents include, but are not limited to, acetate, glutamate, citrate, tartrate, benzoate, lactate, gluconate, phosphate and glycine. A preferred buffering agent comprises a combination of sodium acetate and glacial acetic acid.

The pharmaceutical compositions of the invention typically are aqueous. Such aqueous pharmaceutical compositions may further comprise a pharmaceutically acceptable co-solvent to assist in solubilization of the S-isomer of esmolol or pharmaceutically acceptable salt thereof. Alternatively, the pharmaceutical compositions of the invention may be solvent-based comprising one or more pharmaceutically acceptable solvents. Examples of pharmaceutically acceptable solvents (and co-solvents) include but are not limited to ethanol, isopropanol, ethyl acetate, acetic acid, and ethanolamine.

Suitable osmotic-adjusting agents are known in the art, and are typically present in the pharmaceutical compositions according to the invention in an amount ranging from 1-500 mg/mL. Exemplary osmotic-adjusting agents include, but are not limited to, sodium chloride, dextrose, sodium bicarbonate, calcium chloride, potassium chloride, sodium lactate, Ringer's solution and lactated Ringer's solution. Preferred osmotic adjusting agents include sodium chloride and/or dextrose. Ready-to-use formulations may contain 1-100 mg/mL osmotic-adjusting agent, for example, 3-60 mg/mL sodium chloride or 3-10 mg/mL sodium chloride. Concentrated formulations intended for dilution may contain 1-500 mg/mL or 50-500 mg/mL osmotic-adjusting agent.

Procedures for filling pharmaceutical compositions of the present invention in containers, and their subsequent processing are known in the art. These procedures are conventionally used to produce sterile pharmaceutical drug products often required for health care. Such processing techniques preferably use a sterilization process to destroy or eliminate any microorganisms that may be present in the pharmaceutical composition comprising (S)-methyl-3-[4-(2-hydroxy-3-isopropylamino) propoxy]phenylpropionate or pharmaceutically acceptable salt thereof following preparation and/or packaging of the pharmaceutical compositions. For example, terminal sterilization can be used to destroy all viable microorganisms within the final, sealed package containing the pharmaceutical composition. An autoclave is commonly used to accomplish terminal heat-sterilization of drug products in their final packaging.

Typical autoclave cycles in the pharmaceutical industry to achieve terminal sterilization of the final product are 121° C. for 15 minutes. The composition comprising the S-isomer of esmolol of the present invention can be autoclaved at a temperature ranging from 115° C. to 130° C. for a period of time ranging from 5 to 40 minutes without causing substantial degradation of the (S)-methyl-3-[4-(2-hydroxy-3-isopropylamino) propoxy]phenylpropionate or pharmaceutically acceptable salt thereof. Autoclaving is preferably carried out in the temperature range of 119° C. to 122° C. for a period of time ranging from 10 to 36 minutes.

Alternatively, sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampul, bag, bottle, or syringe) are then filled under aseptic conditions.

As explained above, the methods of the invention are particularly pertinent to the treatment of patients in need of beta blockade and who are susceptible to hypotension. Thus, patients prone to hypotension are particularly suited for treatment by the disclosed methods. By administering a composition comprising S-esmolol in accordance with the invention to patients susceptible to hypotension, the patients receive the beta-blocking benefits of esmolol while minimizing the hypotension that often occurs following administration of the racemic mixture of esmolol. Cardiac conditions that benefit from treatment with a beta blocker include, but are not limited to, tachycardia (e.g., supraventricular tachycardia, intraoperative and postoperative tachycardia) and hypertension (e.g., intraoperative and postoperative hypertension). Moreover, the methods of the invention can also be used to control an elevated heart rate in a patient, when clinically desirable, whether or not the patient has one of the aforementioned cardiac conditions. Conditions that render subjects in need of beta-blockade susceptible to hypotension are particularly pertinent for the methods of the invention are described below.

In various embodiments, subjects treated according to the methods of the invention are in need of beta blockade and are susceptible to hypotension. Subjects are susceptible to hypotension for a variety of reasons including, but not limited to, situations when administration of a relatively high therapeutic dose of racemic esmolol hydrochloride is indicated (e.g., an infusion rate of a pharmaceutical composition comprising racemic esmolol hydrochloride of greater than or equal to 200 µg/kg/min, greater than or equal to 250 µg/kg/min of the racemic mixture, greater than or equal to 300 µg/kg/min of the racemic mixture, greater than or equal to 400 µg/kg/min of the racemic mixture, greater than or equal to 500 µg/kg/min, greater than or equal to 750 µg/kg/min, and/or greater than or equal to 1000 µg/kg/min, for example, an amount between 200 µg/kg/min and 1000 µg/kg/min of racemic esmolol hydrochloride), advanced age, genetic abnormalities, hypovolemia, and diabetic and pre-diabetic conditions. Because preferred doses of racemic esmolol for treating tachycardias are well known in the art, appropriate doses of compositions comprising the S-isomer of esmolol may be easily determined by standard methods.

For example, when relatively high infusion rates of the racemic mixture of esmolol are indicated and administered to humans (e.g., amounts greater than or equal to 200 µg/kg/min of the racemic mixture, greater than or equal to 250 µg/kg/min of the racemic mixture, greater than or equal to 300 µg/kg/min of the racemic mixture, greater than or equal to 400 µg/kg/min of the racemic mixture, greater than or equal to 500 µg/kg/min of the racemic mixture, greater than or equal to 750 µg/kg/min of the racemic mixture, and/or greater than or equal to 1000 µg/kg/min of the racemic mixture), such subjects are particularly susceptible to hypotension. Thus, in various embodiments, the subjects treated according to the methods of the invention can receive relatively high therapeutic doses of the S-isomer of esmolol hydrochloride, e.g., an infusion rate of the S-isomer of esmolol or pharmaceutically acceptable salt of greater than or equal to 0.3 µmol/kg/min (e.g., 100 µg/kg/min S-isomer esmolol hydrochloride), greater than or equal to 0.45 µmol/kg/min (e.g., 150 µg/kg/min S-isomer esmolol hydrochloride), greater than or equal to 0.75 µmol/kg/min (e.g., 250 µg/kg/min S-isomer esmolol hydrochloride), greater than or equal to 1.125 µmol/kg/min (e.g., 375 µg/kg/min S-isomer esmolol hydrochloride), and/or greater than or equal to 1.5 µmol/kg/min (e.g., 500 µg/kg/min S-isomer esmolol hydrochloride), for example, an amount between 0.3 µl mol/kg/min and 1.5 µl mol/kg/min, to achieve greater and more immediate therapeutic effect while minimizing the hypotensive effects often associated with administration of the corresponding doses (here, corresponding infusion rates) of the racemic mixture of esmolol hydrochloride, as compared to the equitherapeutic amount of the S-isomer esmolol hydrochloride.

Additionally, patients of advanced age are known to be susceptible to hypotension. Thus, in various embodiments, the patients in need of treatment are in need of beta blockade and are age 65 or older.

Patients suffering from orthostatic hypotension are also susceptible to developing hypotension as a result of receiving esmolol. Orthostatic hypotension is defined as a condition in which a patient moves from a generally supine position to a generally upright position and experiences an accompanying drop in blood pressure. Therefore, in other embodiments, the patient in need of treatment by the methods of the invention is in need of beta blockade and suffers from, or is prone to, episodes of orthostatic hypotension. Moreover, episodes of orthostatic hypotension occur more frequently in adults age 65 and older. See Benvenuto and Krakoff, *Am J Hypertens* (2010). Thus, in some embodiments the patient in need of treatment by the methods of the invention is age 65 or older and has a history of orthostatic hypotensive episodes.

Patients with diabetes have a higher risk of orthostatic hypotension and thus are susceptible to developing hypotension. See Wu et al., *Diabetes Care*, 32:1, 69-74 (2009). In some embodiments, the patient in need of treatment by the methods of the invention suffers from type I diabetes, type II diabetes, or are considered to have "pre-diabetes," a condition in which an individual's blood glucose levels are elevated, but not as much as individuals having diabetes. Glucose levels are generally determined by using a Fasting Plasma Glucose Test (FPG) or an Oral Glucose Tolerance Test (OGTT), but other tests may also be used.

With the FPG test, a fasting blood glucose level between 100 and 125 milligrams per deciliter (mg/dL) is indicative of pre-diabetes, and a fasting blood glucose level of 126 mg/dL or higher is indicative of diabetes. With the OGTT test, an individual's blood glucose level is measured two hours after drinking a glucose-rich beverage. A two-hour blood glucose level between 140 and 199 mg/dL is indicative of pre-diabetes, and a two-hour blood glucose level at 200 mg/dL or higher is indicative of diabetes.

Patients suffering from familial orthostatic hypotensive disorder are also susceptible to developing hypotension as a result of receiving esmolol. Familial orthostatic hypotensive disorder is characterized by light-headedness on standing, which may worsen to syncope, palpitations, and blue-purple ankle discoloration, and is accompanied by a marked decrease in systolic blood pressure, an increase in diastolic pressure, and tachycardia, all of which resolve when supine. See DeStefano et al., *AJHG*, 63:5, 1425-1430 (1998). In some embodiments, the patient in need of treatment by the methods of the invention suffers from familial orthostatic hypotensive disorder.

Several genetic abnormalities including, but not limited to, aldosterone deficiency (e.g., Ulick syndrome or Visser syndrome), Algrove syndrome, tetrahyrdobiopterin deficiency, aromatic L-amino acid decarboxylase deficiency, monoamine oxidase deficiency, dopamine-β-hydroxylase deficiency, Biaggioni syndrome, Menkes syndrome (trichopolydystrophy), familial dysautonomia (Riley-Day syndrome), hereditary sensory and motor neuropathies, familial amyloidosis (Andrade syndrome), familial olivopontocerebellar atrophy, mitral valve prolapsed syndrome, hereditary mast cell activation disorder, and Bartter syndrome have been shown to be associated with susceptibility to developing hypotension. See Robertson, *Curr Opin Nephrol Hypertens*, 3(1):13-24 (1994). Thus, in various embodiments, the patient in need of treatment by the methods of the invention suffers from one or more disorders selected from the group consisting of aldosterone deficiency (e.g., Ulick syndrome or Visser syndrome), Algrove syndrome, tetrahyrdobiopterin deficiency, aromatic L-amino acid decarboxylase deficiency, monoamine oxidase deficiency, dopamine-β-hydroxylase deficiency, Biaggioni syndrome, Menkes syndrome (trichopolydystrophy), familial dysautonomia (Riley-Day syndrome), hereditary sensory and motor neuropathies, familial amyloidosis (Andrade syndrome), familial olivopontocerebellar atrophy, mitral valve prolapsed syndrome, hereditary mast cell activation disorder, and Bartter syndrome.

Further, hypotension is a common occurrence after induction of general anesthesia. See Reich et al., *Anesth Analg*, 101:3, 622-628 (2005). Thus, in some embodiments, the patient in need of treatment by the methods of the invention is in need of beta blockade and is either undergoing a procedure under general anesthesia, or was administered general anesthesia within the last 36 hours. Similarly, hypotension is one of the most frequent side effects of spinal anesthesia. See Hartmann et al., *Anesthesia & Analgesia*, 94:6, 1521-1529 (2002). In some embodiments, the patient in need of treatment by the methods of the invention is in need of beta blockade and is either undergoing a procedure under spinal anesthesia or was administered spinal anesthesia within the last 36 hours.

In a study analyzing the potential of bisoprolol (a beta blocker) as an agent to protect patients at risk for cardiovascular complications undergoing surgery with spinal block, researchers identified a polymorphism in the ADRB2 gene as a predictor of hypotension. See Zaugg, *Anesthesiology*, 107: 33-44 (2007). Zaugg et al. found that individuals with the Gly16Arg polymorphism (refSNP ID: rs1042713; SEQ ID NO: 1) were more likely to experience hypotension following administration of bisoprolol. Thus, in some embodiments, the patient in need of treatment by the methods of the invention is in need of beta blockade and carries the ADRB2 Gly16Arg polymorphism.

Additionally, it is known that patients of Asian ancestry are more susceptible to esmolol-induced hypotension. See Ko et al., *JACC* 23:302-6 (1994). Using the manufacturer-recommended loading infusion of 500 μg/kg body weight per minute, Ko et al. found that all patients administered this dosage experienced acute hypotension. Id. at 303. Only by lowering the loading dose and maintenance dose were the researchers able to control supraventricular tacharrhythmia without causing hypotension. Id. at 302. Thus, in some embodiments, the patient in need of treatment by the methods of the invention is in need of beta blockade and is of Asian ancestry, for example, the patient can be of Chinese ancestry.

EXAMPLES

The following examples are provided for illustration and are not in any way to limit the scope of the invention.

Table 1 lists properties of the esmolol composition utilized in the following studies. "Batch number" refers to the intended concentration of esmolol hydrochloride. "Actual Esmolol concentration" refers to the actual concentration of esmolol hydrochloride in each particular formulation as determined by a non-chiral HPLC method at the time the formulation was prepared ("pre-animal testing") or after animal testing ("post-animal testing") as indicated below. A chiral HPLC method was used to determine the ratio of S-isomer to R-isomer in the compositions. The actual esmolol concentrations determined pre-animal testing were used to determine animal dosing. The small concentration variance between pre-animal testing and post-animal testing values demonstrates the stability of the compositions. The pH of each formulation was determined pre-animal testing and post-animal testing. Osmolality was determined post-animal testing.

TABLE 1

| | | Composition | | | | | | Testing | | |
|---|---|---|---|---|---|---|---|---|---|---|
| Batch number | Isomer | Actual Esmolol concentration (pre-animal testing) | Actual Esmolol concentration (post-animal testing) | Ratio S-isomer: R-isomer | Sodium Chloride | Sodium Acetate | Acetic Acid | pH (pre-animal testing) | pH (post-animal testing) | Osmolality (mOsm/kg) |
| 10 | S-Isomer | 8.98 mg/mL | 8.97 mg/mL | 99.4:0.6 | 5.9 mg/mL | 2.8 mg/mL | 0.546 mg/mL | 4.91 | 4.87 | 304 |
| 20 | Racemate | 20.48 mg/mL | 20.52 mg/mL | 50:50 | 4.1 mg/mL | 2.8 mg/mL | 0.546 mg/mL | 4.88 | 4.83 | 299 |
| 25 | S-Isomer | 21.72 mg/mL | 21.86 mg/mL | 98.5:1.5 | 3.2 mg/mL | 2.8 mg/mL | 0.546 mg/mL | 4.88 | 4.81 | 322 |
| 25 | R-Isomer | 24.88 mg/mL | 25.19 mg/mL | 1.6:98.4 | 3.2 mg/mL | 2.8 mg/mL | 0.546 mg/mL | 4.98 | 4.91 | 299 |

Example 1

Establishment of a Model System to Analyze the Contribution of Esmolol Enantiomers to Hypotension A model system utilizing anesthetized mongrel dogs was established in order to predict the hypotensive potential of esmolol hydrochloride injection in human patients. One dog was administered a formulation containing racemic esmolol hydrochloride at a loading dose of 600 µg/kg/min for 3 minutes followed by a maintenance infusion of 300 µg/kg/min for 10 minutes (referred to as 600RS/300RS) followed by a washout period (FIG. 1). In this and subsequent figures, the duration of infusion of the various medicaments is indicated by a coded horizontal line, parallel to the time axis. This protocol was repeated by administering 2000 µg/kg/min for 3 minutes followed by a maintenance infusion of 1000 µg/kg/min for 10 minutes (referred to as 2000RS/1000RS) and then by administering 400 µg/kg/min for 3 minutes followed by a maintenance infusion of 200 µg/kg/min for 10 minutes (referred to as 400RS/200RS). Mean arterial blood pressure and heart rate were monitored throughout the experiment. There was a clear dose-dependent decrease in mean arterial blood pressure in response to administration of the racemic formulation of esmolol hydrochloride, which was accompanied by a dose-dependent reflex tachycardia. While esmolol administration is normally expected to reduce heart rate, similar reflex tachycardia have been reported in humans secondary to hypotension at esmolol doses of 500 µg/kg/min and higher See Reilly et al., *Clin Pharmacol Ther.* 38:579-85 (1985).

These data indicate that the mongrel dog is a relevant species for evaluating the hypotensive potential of different formulations of esmolol hydrochloride in part because humans are known to similarly exhibit hypotension (or a hypotensive response) in response to racemic esmolol hydrochloride treatment. While the doses administered to the dogs in the experiments described herein were larger than typical clinical doses, the doses were administered in order to increase repeatability and induce acute hypotension in close to 100% of the dogs by sufficiently increasing the effect level above background noise. Moreover, relative to esmolol administration in humans, the dog model replicates within experimental error the same dependence of mean arterial blood pressure versus infusion rate. Therefore, the conclusions reached at these relatively higher dose levels in dogs are relevant to minimization of adverse effects at lower doses in humans.

Example 2

A Composition Comprising the S-Isomer of Esmolol Demonstrates Decreased Hypotensive Potential Relative to the Racemic Formulation The animal model of Example 1 allowed comparison of compositions comprising the S-isomer of esmolol and compositions comprising the racemic mixture of esmolol in a complex biological system. While beta blockers are often manufactured and commercialized as the RS racemic mixture, the S-isomer is responsible for all of the beta blocking activity. See Mehvar and Brocks, *J. Pharm Pharmaceut Sci,* 482:185-200 (2001). Thus, the S-isomer of esmolol is about twice as potent as a beta-adrenergic-blocking agent than an equivalent amount of the racemic mixture. See International Patent Publication No. WO 88/01614. In view of the foregoing, the experiments described herein illustrate administration of compositions comprising the racemic mixture of esmolol relative to compositions comprising the S-isomer of esmolol, in which the administered amount of S-isomer was half the amount of the racemic mixture. Because the S-isomer possesses substantially all of the therapeutic potential present in the racemic mixture, compositions comprising half the amount of the S-isomer were considered equitherapeutic to compositions comprising a given amount of the racemic mixture of esmolol. In other words, when 600 µg/kg/min of the composition comprising racemic esmolol was administered, the equitherapeutic dose/infusion rate of the composition comprising S-isomer administered for direct comparison was 300 µg/kg/min.

In initial experiments, the hypotensive potential of a composition comprising the S-isomer of esmolol hydrochloride was compared to a composition comprising the racemic formulation. Mean arterial blood pressure, cardiac output, and systemic vascular resistance were monitored throughout the experiments. Cardiac output and systemic vascular resistance were evaluated to understand the cause of the hypotension (i.e., decrease in cardiac output and/or decrease in systemic vascular resistance).

Each of four mongrel dogs was administered increasing doses of esmolol hydrochloride (FIGS. 2-5). Two dogs (D00028 and DG0029) received 150 µg/kg/min of the S-isomer formulation until mean arterial pressure reached a steady state, at which time the animal was immediately switched over to 300 µg/kg/min of the racemic formulation (this protocol is referred to as 150S/300RS in FIGS. 3a and 4a). Once a steady state was reached the infusion was stopped and was followed by a washout period. A similar protocol was repeated in both dogs using 300 µg/kg/min of the S-isomer of esmolol followed by administration of 600 µg/kg/min of the racemic mixture of esmolol (this protocol is 300S/600RS in FIGS. 3b and 4b). A final protocol involved administration of 1000 µg/kg/min of the S-isomer of esmolol followed by administration of 2000 µg/kg/min of the racemic mixture of esmolol followed by 1000 µg/kg/min of the S-isomer of esmolol (this protocol is referred to as 1000S/2000RS/1000S in FIGS. 3c and 4c).

A similar series of protocols were repeated with the other two dogs (DG0027 and DG0030) except the racemic mixture of esmolol was administered before the S-isomer. In other words, 300 µg/kg/min of the racemic mixture of esmolol was administered, followed by administration of 150 µg/kg/min of the S-isomer of esmolol (this protocol is referred to as 300RS/150S in FIGS. 2a and 5a), 600 µg/kg/min of the racemic mixture of esmolol was administered, followed by administration of 300 µg/kg/min of the S-isomer of esmolol (this protocol is referred to as 600RS/300S in FIGS. 2b and 5b), and 2000 µg/kg/min of the racemic mixture of esmolol was administered, followed by administration of 1000 µg/kg/min of the S-isomer of esmolol, and then 2000 µg/kg/min of the racemic mixture of esmolol again (this protocol is referred to as 2000RS/1000S/2000RS in FIGS. 2c and 5c)].

Figure 3A:
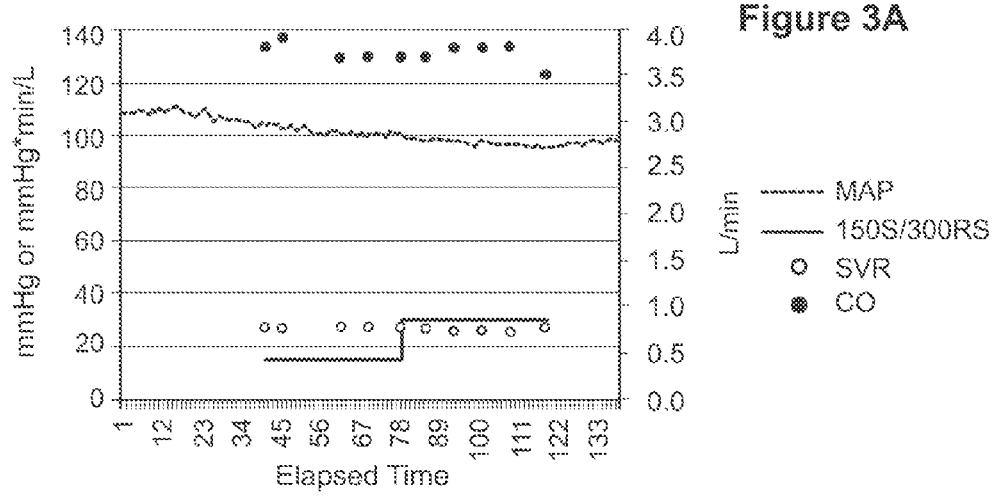
FIGS. 3A-3C illustrate the results of experiments to evaluate the effects of administering pharmaceutical compositions comprising racemic mixtures of esmolol as compared to pharmaceutical compositions comprising the S-isomer of esmolol.
Figure 3B:
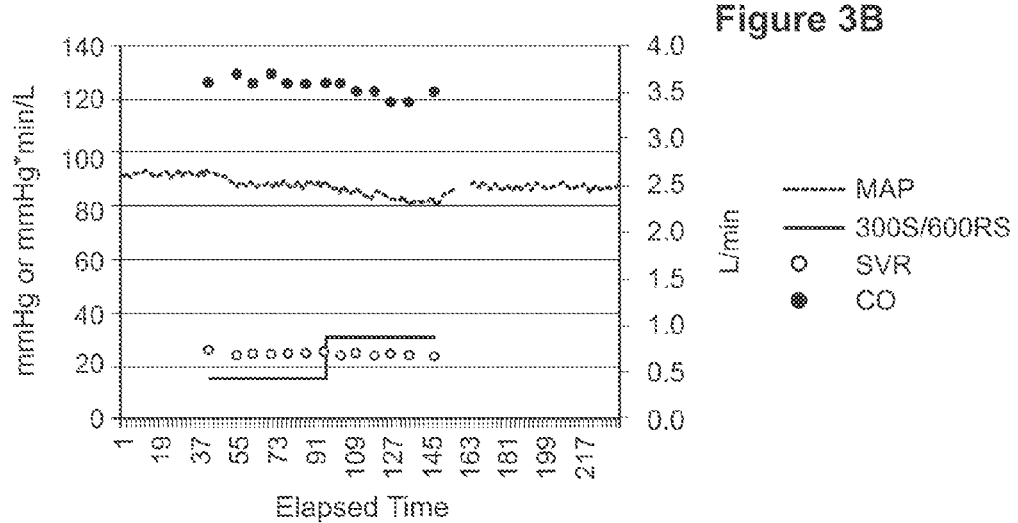
Figure 3C:
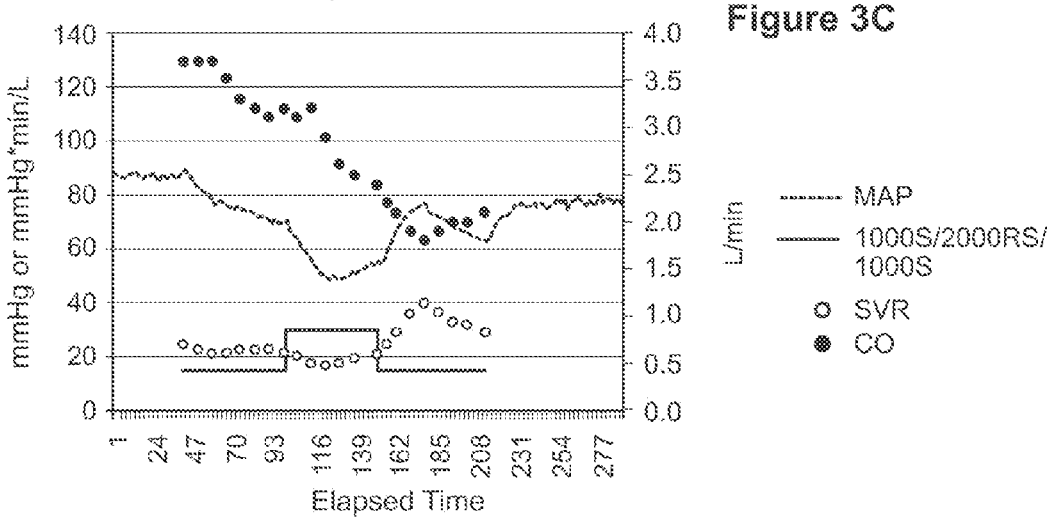
Figure 4A:
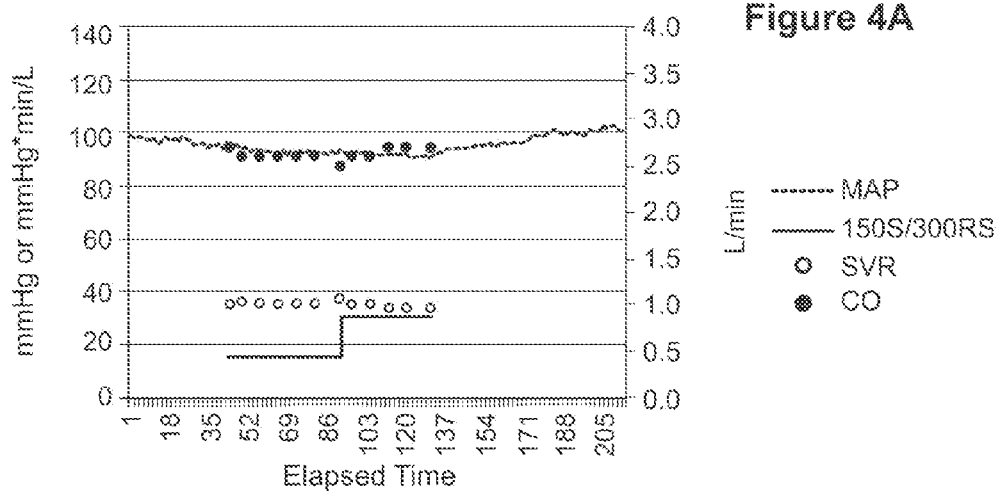
FIGS. 4A-4C illustrate the results of experiments to evaluate the effects of administering pharmaceutical compositions comprising racemic mixtures of esmolol as compared to pharmaceutical compositions comprising the S-isomer of esmolol.
Figure 4B:
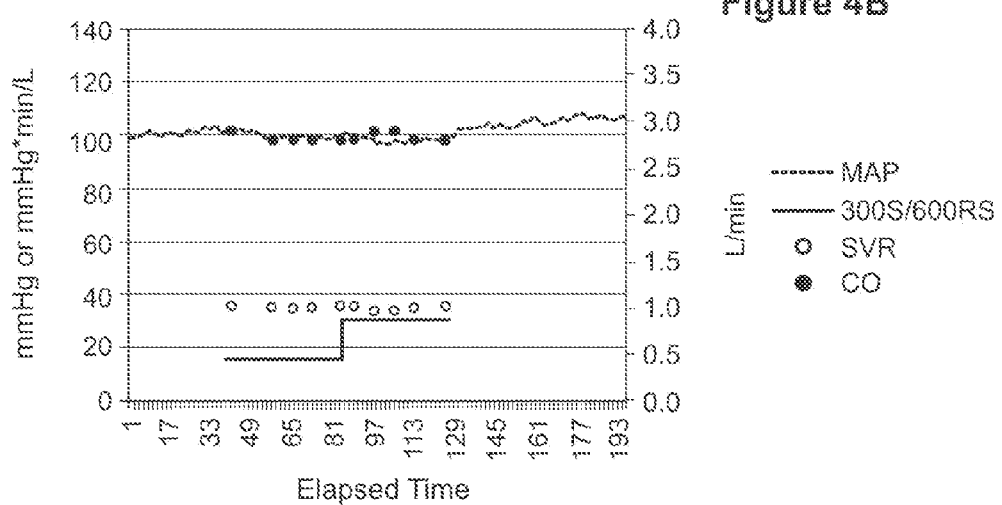
Figure 4C:
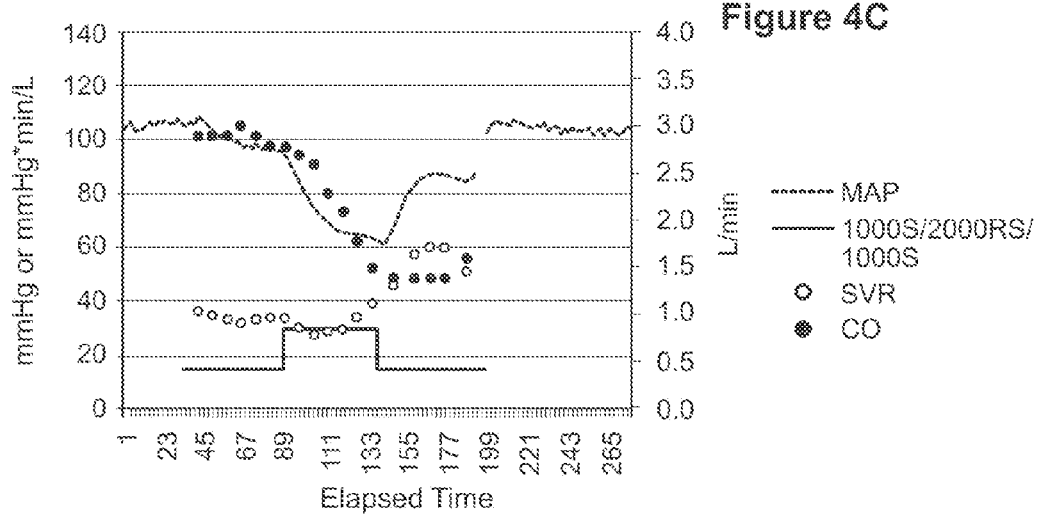
Figure 5A:
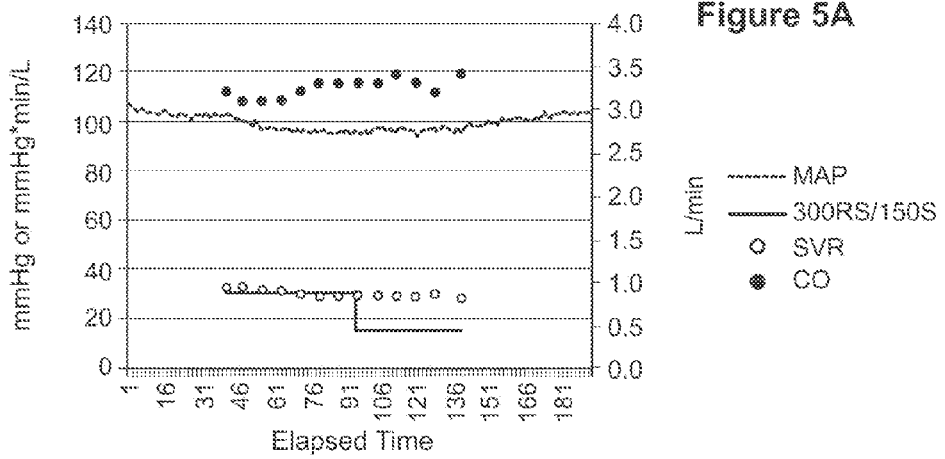
FIGS. 5A-5C illustrate the results of experiments to evaluate the effects of administering pharmaceutical compositions comprising racemic mixtures of esmolol as compared to pharmaceutical compositions comprising the S-isomer of esmolol.
Figure 5B:
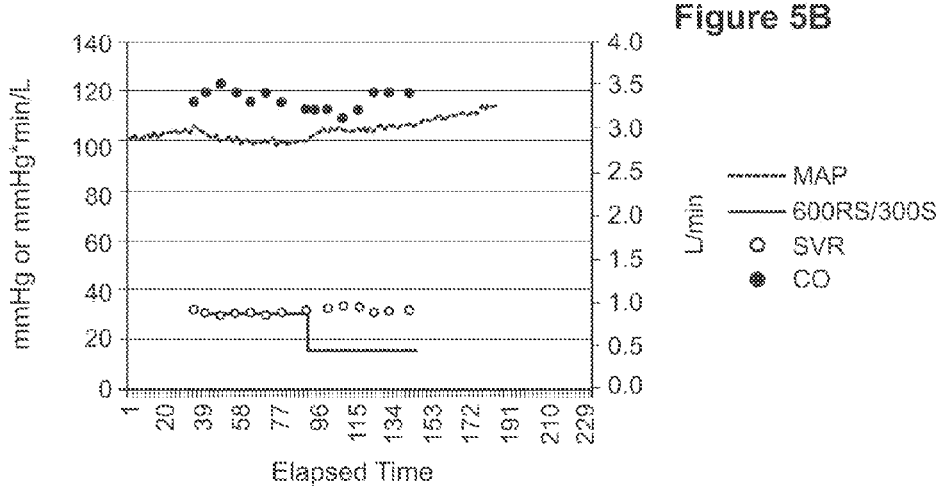
Figure 5C:
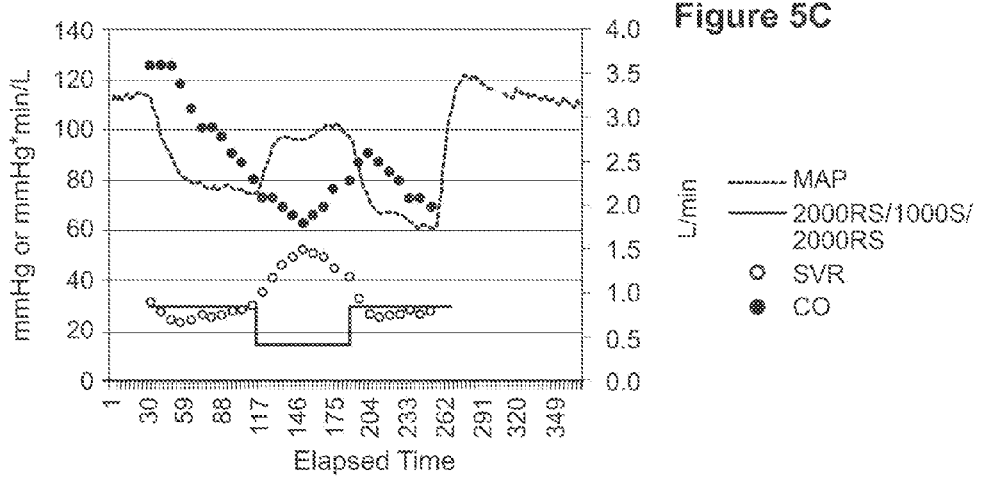

Similar to Example 1, the racemic formulation caused a dose-dependent decrease in mean arterial pressure in all four dogs regardless of whether it was administered before or after administration of the S-isomer. At the high dose infusion protocol, there was an unequivocal difference in mean arterial blood pressure between the two formulations. Specifically, the S-isomer produced significantly less hypotension relative to the racemic formulation. In general, the differentiation between the S-isomer and racemic formulations on mean arterial blood pressure was apparent at the middle infusion protocol in which 300 µg/kg/min S-isomer and 600 µg/kg/min of the racemic mixture were administered (see FIGS. 2b and 5b; FIGS. 3b and 4b). Thus, differentiation is apparent at a dose of the racemic mixture which is only approximately two- to three-fold higher than the most clinically relevant infusion rate (i.e., 200 µg/kg/min of the racemic mixture) in humans. During the 2000RS/1000S/2000RS administration protocol, mean arterial blood pressure increased during the 1000S phase (see FIG. 2c). These data indicate that the R-isomer is contributing to the hypotensive potential of the racemic formulation.

Example 3

Compositions Comprising the S-Isomer of Esmolol Exhibit Similar Efficacy with Less Hypotension Relative to Racemic Formulations The purpose of this experiment was to determine if the attenuated hypotension (as assessed by mean arterial blood pressure end point) observed in Example 2 following administration of the S-isomer was associated with reduced efficacy (i.e., ability to control isoproterenol-induced tachycardia) as compared with the racemic formulations.

Figure 6A:
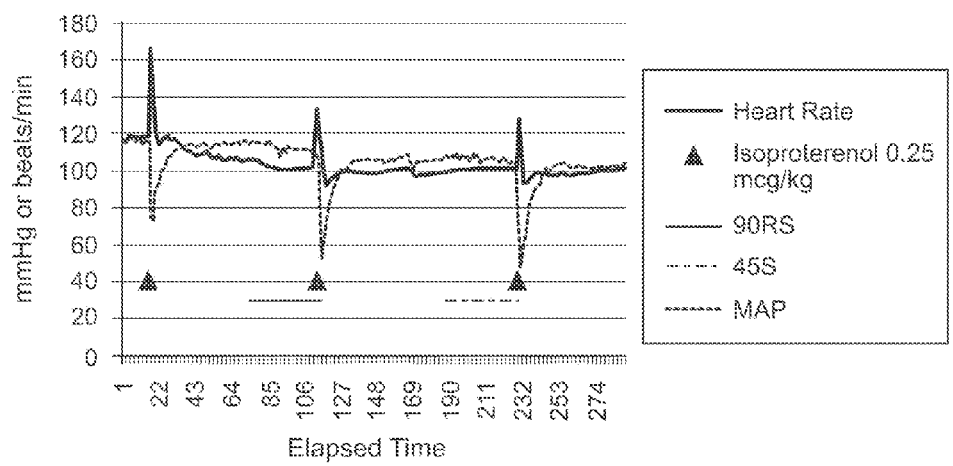
Figure 6B:
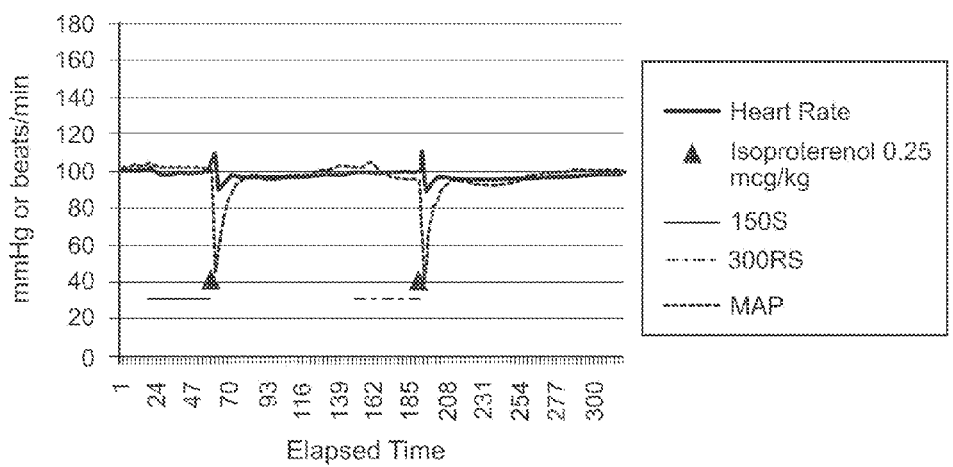

One dog was administered a bolus dose of isoproterenol (0.25 µg/kg) to establish a baseline heart rate response (FIG. 6a). Isoproterenol is a non-selective β1 adrenergic agonist capable of inducing tachycardia. After a washout period, the racemic formulation (RS) was administered at 90 µg/kg/min for 10 minutes immediately followed by an isoproterenol challenge. After a washout period, the S-isomer formulation (S) was administered at 45 µg/kg/min for 10 minutes immediately followed by another isoproterenol challenge. This protocol was repeated using 150 µg/kg/min S-isomer followed by 300 µg/kg/min racemic formulation (FIG. 6b) then 2000 µg/kg/min racemic formulation followed by 1000 µg/kg/min S-isomer (FIG. 6c). Similar to Example 2, the racemic formulation caused a greater dose-dependent decrease in mean arterial blood pressure relative to the S-isomer.

At the high infusion rate, there was a significant difference in the mean arterial blood pressure response between the two formulations. Specifically, the S-isomer produced significantly less hypotension relative to the racemic formulation. As the infusion rate of esmolol increased, a dose-dependent decrease in heart rate was observed following the isoproterenol challenge. The observed dose-dependent decrease in heart rate is expected, as the number of available receptors for isoproterenol to interact with decreases as the dose of esmolol increases. More importantly, equitherapeutic amounts of the S-isomer consistently demonstrated the same degree of efficacy in reducing isoproterenol-induced tachycardia as compared with the racemic formulation. In total, this data indicates that the S-isomer exhibits similar efficacy (heart rate end point) with less hypotension (mean arterial blood pressure end point) as compared with the racemic formulation over a very broad range of infusion rates.

Example 4

Figure 8A:
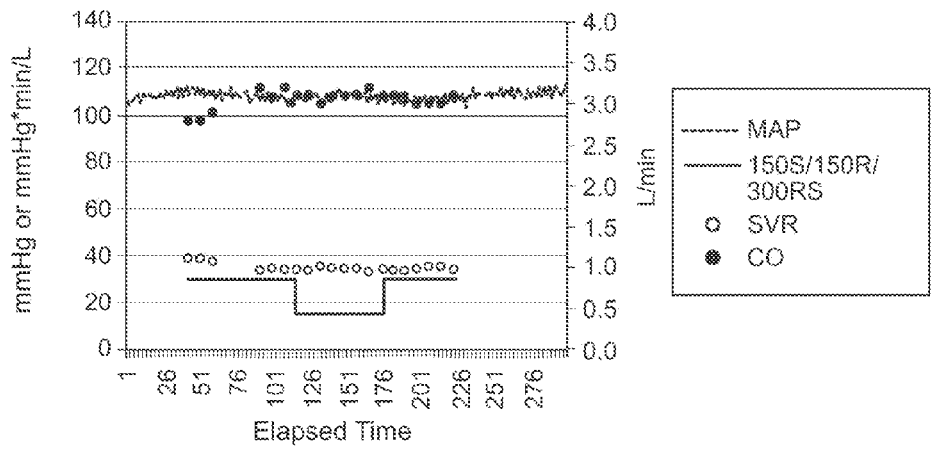
FIGS. 8A and 8B illustrate the results of experiments to evaluate the effects of administering pharmaceutical compositions comprising racemic mixtures of esmolol as compared to pharmaceutical compositions comprising the R-isomer of esmolol and pharmaceutical compositions comprising the S-isomer of esmolol.
Figure 8B:
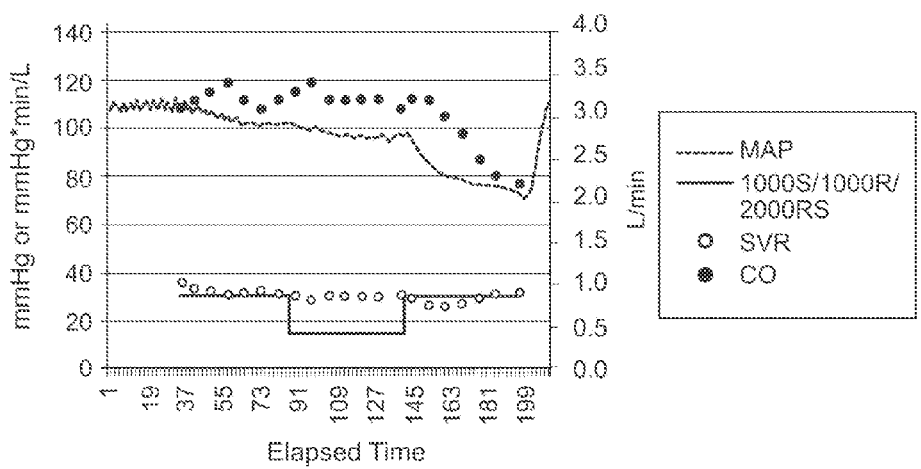
Figure 9A:
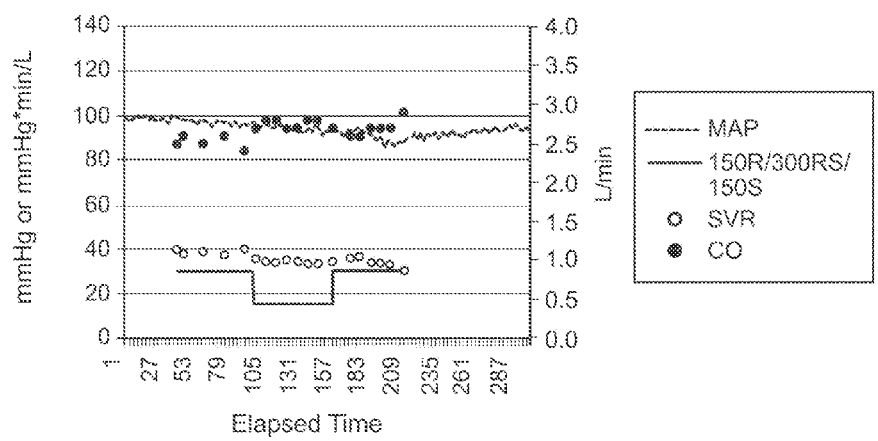
FIGS. 9A and 9B illustrate the results of experiments to evaluate the effects of administering pharmaceutical compositions comprising racemic mixtures of esmolol as compared to pharmaceutical compositions comprising the R-isomer of esmolol and pharmaceutical compositions comprising the S-isomer of esmolol.
Figure 9B:
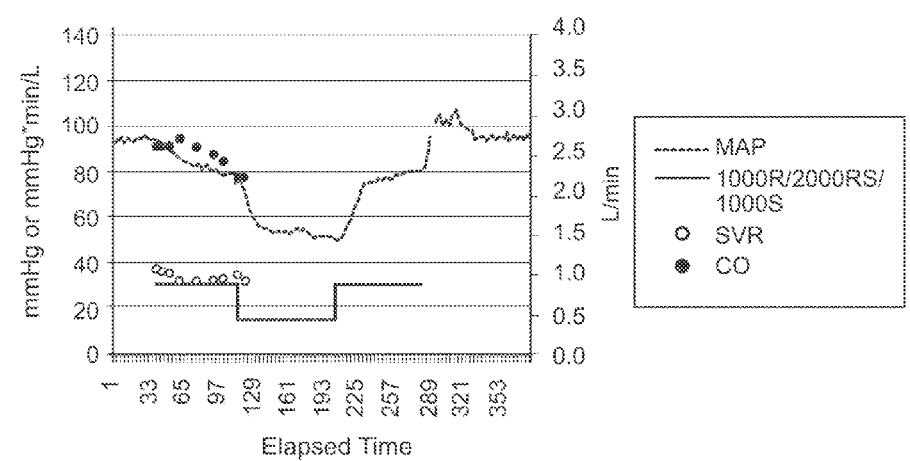

The S-isomer of esmolol produces significantly less hypotension as compared with the racemic and the R-isomer formulations The hypotensive potential of an R-isomer only formulation of esmolol hydrochloride was compared to the S-isomer and racemic formulations. Each of three mongrel dogs was administered all three formulations using a Latin-square design at each of two infusion rates (FIGS. 7-9). For example, animal DG0024 received 300 µg/kg/min of the racemic formulation for 10 minutes, at which time the animal was immediately switched over to 150 µg/kg/min of the S-isomer formulation for 10 minutes, at which time the animal was immediately switched over to 150 µg/kg/min of the R-isomer formulation for 10 minutes (this protocol is referred to as 300RS/150S/150R in FIG. 7a) followed by a washout period. This protocol was repeated in animal DG0024 using the high infusion rate protocol (i.e., 2000 µg/kg/min of the racemic formulation for 10 minutes, 1000 µg/kg/min of the S-isomer for 10 minutes, 2000 µg/kg/min of the racemic formulation for 10 minutes; this protocol is referred to as 2000RS/1000S/1000R in FIG. 7b). The treatment sequence and monitored parameters for animals DG0032 and DG0033 are depicted in FIGS. 8a and 8b and FIGS. 9a and 9b, respectively.

At the low infusion rate, there were no observed differences in mean arterial blood pressure between the three formulations. This finding is consistent with the findings from Example 2, indicating that differentiation between the S-isomer and the racemic formulations do not manifest in dogs until infusion rates are approximately 300 µg/kg/min for the S-isomer of esmolol and 600 µg/kg/min for the racemic mixture.

At the high dose infusion rate, there was a salient difference in mean arterial blood pressure following the S-isomer formulation as compared with the racemic formulation. Specifically, mean arterial blood pressure improved (or increased) following infusion of the S-isomer formulation relative to the racemic formulation. This finding is also consistent with that observed in Example 2, above.

Figure 10:
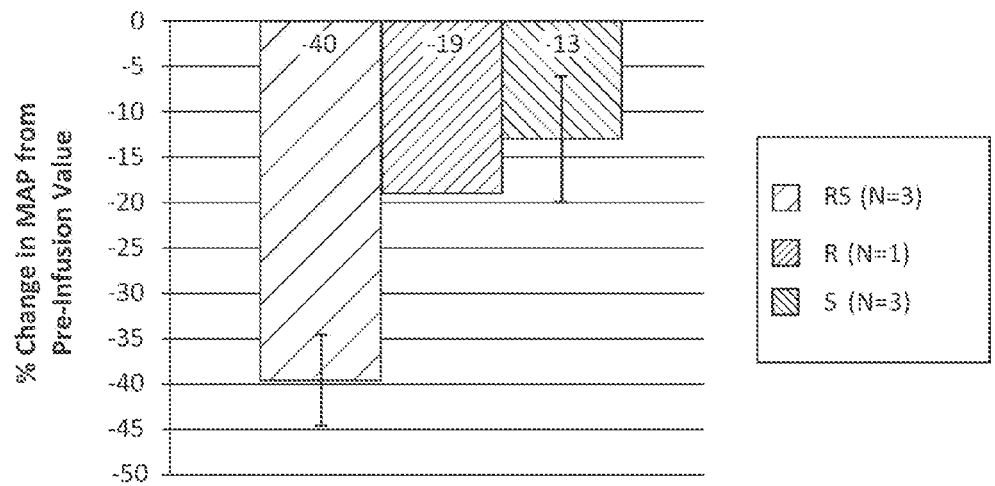
FIG. 10 illustrates the results of experiments comparing the hypotensive response after administering pharmaceutical compositions comprising racemic mixtures of esmolol as compared to pharmaceutical compositions comprising the R-isomer of esmolol and pharmaceutical compositions comprising the S-isomer of esmolol. The results displayed are the averages of the percent change in mean arterial pressure from a resting baseline state, just prior to beginning a particular infusion to the end of a particular infusion.

The individual animal data from the high dose infusion protocols of FIGS. 2-5 and 7-9 were combined and are presented in FIG. 10. The change in mean arterial pressure (MAP) from pre-infusion (i.e., resting baseline state just prior to beginning a particular infusion) values is depicted as a percent change calculated as follows: [((value at the end of the infusion-value at the start of infusion)/value at the start of infusion)*100]. Based on these data, starting from baseline, administration of the RS racemic mixture decreases MAP by 40%, while administration of the S-isomer formulation decreases it by only 13%. Interestingly, the effect of administration of the R-isomer formulation lies between these values, resulting in a 19% decrease. The sum of the effects of R-isomer and S-isomer formulation administration is substantially equivalent to the effect of RS administration, which is consistent with the relative infusion rates of the drugs in these experiments: 1000 µg/kg/min R and 1000 µg/kg/min S, and 2000 µg/kg/min RS.

Figure 11:
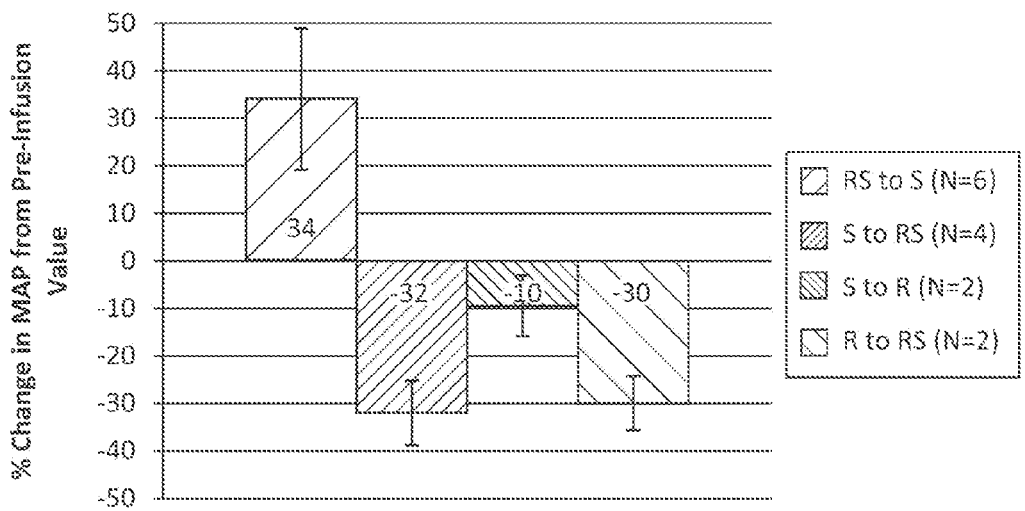
FIG. 11 illustrates the results of experiments comparing the change in mean arterial pressure when immediately transitioning from administration of one pharmaceutical composition to another. The results displayed are the averages of the percent change in mean arterial pressure from the end of the first infusion to the end of the second infusion.

The effect of starting from different initial states upon MAP is shown in FIG. 11. Thus, starting from an initial state where the RS racemic mixture has been administered, MAP actually increases 34% upon administration of the S-isomer, thereby demonstrating that administration of the S-isomer formulation causes recovery from the hypotensive effect induced by administration of the racemic mixture. On the other hand, starting from an initial state where the animal has been administered the S-isomer formulation, subsequent administration of the RS racemic mixture formulation decreases MAP by 32%, an almost equivalent amount in the reverse direction of the RS to S experiment.

The cardiovascular changes following administration of the R-isomer formulation were qualitatively identical to those following the administration of the racemic formulation. These data indicate that the R-isomer is contributing to the cardiovascular changes observed following the racemic formulation, including the decrease in mean arterial blood pressure (i.e., hypotension). Taken together, the data from Examples 1-4 indicate that the R-isomer appears to contribute significantly to the hypotension observed with administration of the racemic mixture with no apparent, inherent ability to lower heart rate when experimentally increased.

Example 5

Compositions Comprising the S-Isomer of Esmolol Produce Significantly Less Hypotension and Exhibit Similar Efficacy as Compared with Compositions Comprising the Racemic Mixture The purpose of this experiment was to confirm the results of Example 3 demonstrating that the attenuated hypotension (as demonstrated by mean arterial blood pressure end point) following administration of the S-isomer is associated with substantially equivalent efficacy (i.e., ability to control isoproterenol-induced tachycardia) as compared with the racemic formulations by testing a broader range of doses and using an increased number of test subjects than in Example 3.

The experimental protocol was carried out essentially as described in Example 3. In short, each dog was administered racemic esmolol (RS) at the indicated dose for 10 minutes immediately followed by an isoproterenol challenge (a bolus dose of isoproterenol at 0.25 μg/kg). After a washout period, the S-isomer formulation (S) was administered at an equitherapeutic dose for 10 minutes immediately followed by another isoproterenol challenge. This protocol was performed at 90 μg/kg/min RS/45 μg/kg/min S (5 dogs), 300 μg/kg/min RS/150 μg/kg/min S (1 dog), 600 μg/kg/min RS/300 μg/kg/min S (3 dogs), 1000 μg/kg/min RS/500 μg/kg/min S (4 dogs), and 2000 μg/kg/min RS/1000 μg/kg/min S (3 dogs).

Figure 12A:
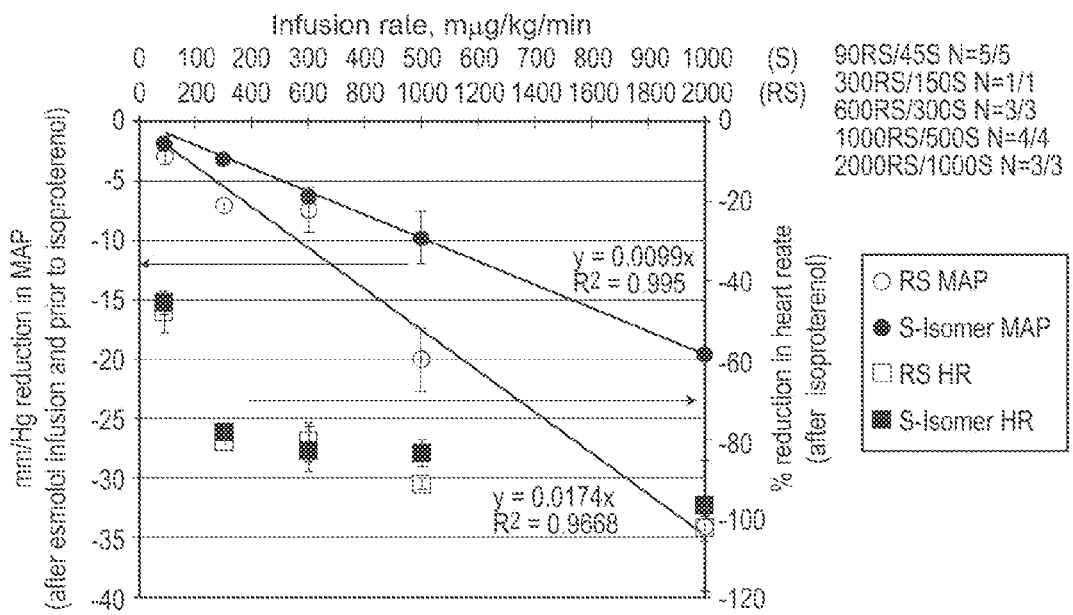
FIGS. 12A and 12B illustrate the results of experiments evaluating the effects of administering pharmaceutical compositions comprising racemic mixtures of esmolol following isoproterenol challenge as compared to pharmaceutical compositions comprising the S-isomer of esmolol following isoproterenol challenge.

FIG. 12A compares the effects on mean arterial blood pressure and heart rate following isoproterenol challenge in dogs receiving infusions of racemic esmolol or the S-isomer at the stated infusion rates. The percent reduction in heart rate was essentially identical when a given dose of racemic esmolol was compared to an equitherapeutic dose of the S-isomer (i.e., a dose of the S-isomer comprising half the amount of the racemic mixture e.g., 90 μg/kg/min racemic esmolol compared to 45 μg/kg/min S-isomer formulation) at all doses. Thus, an S-isomer esmolol formulation administered at half the dose of the racemic formulation is able to produce equivalent therapeutic efficacy (i.e., heart rate reduction). However, the hypotensive effect as determined by the reduction in mean arterial pressure differed significantly at doses greater than 600 μg/kg/min racemic esmolol/300 μg/kg/min S-isomer formulation. For example, the reduction in mean arterial pressure at an infusion rate of 1000 μg/kg/min racemic esmolol was about 20 mmHg while the reduction in mean arterial pressure was about 10 mmHg at an equitherapeutic dose of 500 μg/kg/min of the S-isomer. Thus, the presence of the R isomer in the racemic mixture contributes significantly to the hypotension associated with racemic esmolol. Notably, equitherapeutic doses of the S-isomer consistently demonstrated the same degree of efficacy in reducing isoproterenol-induced tachycardia as compared with the racemic formulation (across all doses).

Figure 12B:
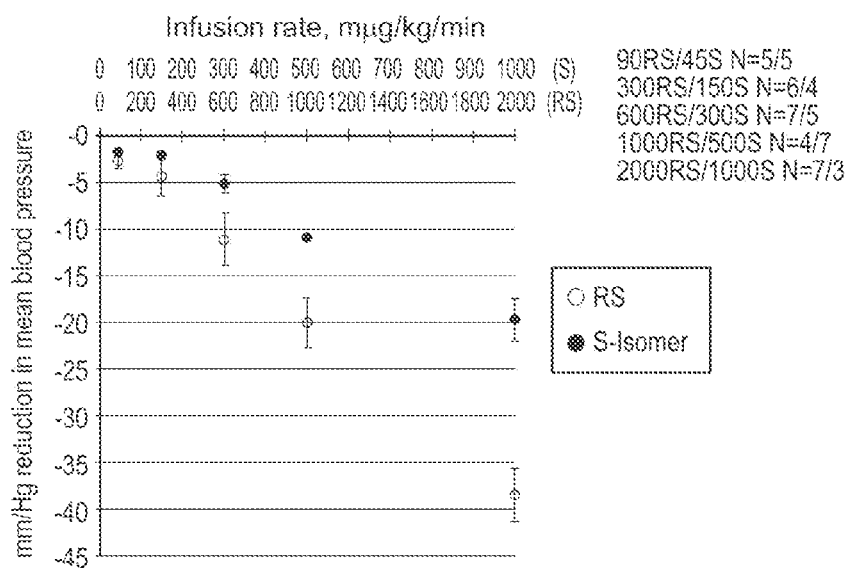

In order to better estimate the true differential effect in hypotensive potential between racemic esmolol and the S-isomer of esmolol at the lower dose range, data from other dogs that were not part of the isoproterenol challenge experiments, but were otherwise treated identically, were combined with the data set from FIG. 12A and presented in FIG. 12B. The additional data points were only from those dogs where a stated dose was administered first or where a sufficient wash-out period preceded the stated dose as to avoid any confounding variables. Increasing the sample size revealed a statistically significant difference in mean arterial pressure at the 600 μg/kg/min racemic esmolol (7 dogs)/300 μg/kg/min S-isomer (5 dogs) dose comparison. Thus, the lack of significant differentiation in mean arterial pressure seen at the lower doses in FIG. 12A was likely due to the relatively smaller sample size and biological variability.

These data demonstrate that an equitherapeutic dose of the S-isomer of esmolol can achieve all of the therapeutic efficacy (i.e., heart rate reduction) of a corresponding dose of racemic esmolol with significantly less hypotension as demonstrated by the respective mean arterial blood pressure changes over a very broad range of infusion rates.

Example 6

The Relevance of the Dog Model to Humans

Figure 13:
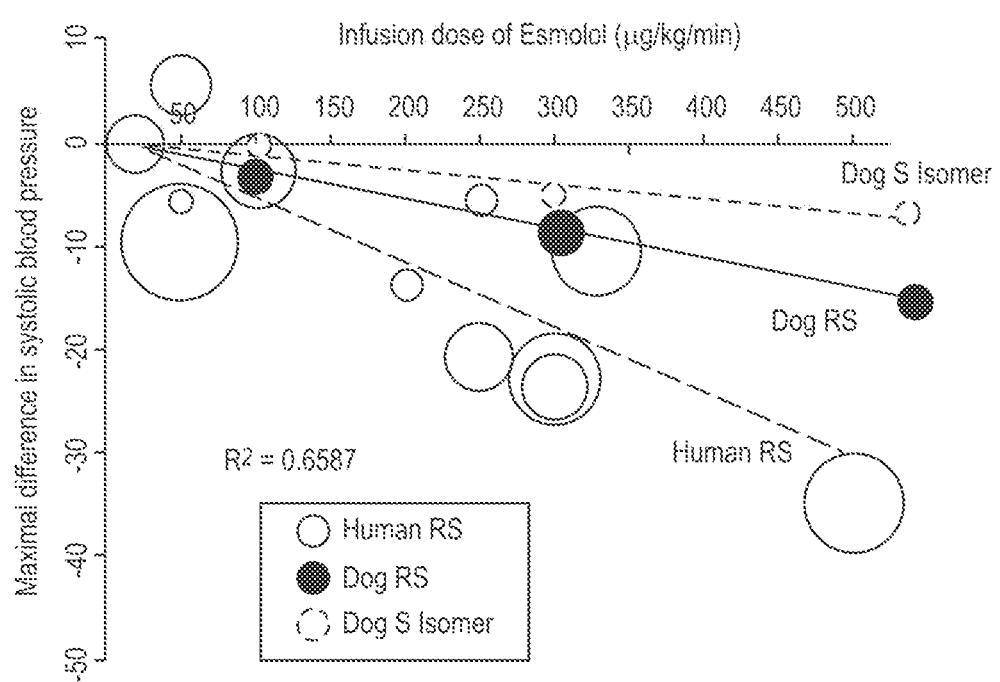
FIG. 13 illustrates the effects of administering pharmaceutical compositions comprising racemic mixtures of esmolol on systolic blood pressure from the aforementioned experiments in dogs as compared with humans.

The esmolol doses administered to the dogs in the experiments described herein needed to be larger than typical clinical doses used in humans in order to increase repeatability and induce acute hypotension in close to 100% of the dogs by sufficiently increasing the effect level above background noise. To confirm that the results obtained herein with mongrel dogs are clinically relevant, data from the experimental results obtained herein were superimposed with the maximal weighted mean difference in systolic blood pressure results obtained by Yu et al. in a meta-analysis of randomized controlled clinical trials with esmolol hydrochloride (Yu et al., *AnesthAnalg.* 2011 February; 112(2):267-81). As is shown in FIG. 13, these data demonstrate that human patients experienced clinical hypotension more than two times as severe as the dog model at a given dose of the racemic mixture of esmolol. Further still, FIGS. 12A and 12B demonstrate that significant differentiation was observed in dogs at a dose of the racemic mixture (i.e., 300 μg/kg/min of the racemic mixture) which is clinically relevant in humans. In view of the greater than two-fold increase in hypotensive effect experienced by humans at a given dose of the racemic mixture of esmolol (relative to an equitherapeutic dose of the S-isomer formulation), these data confirm that the conclusions reached in dogs are relevant to the minimization of adverse effects at even lower clinically relevant doses in humans.

What is claimed:

1. A method for treating tachycardia in a subject, the method comprising:

administering to the subject a therapeutically effective amount of a pharmaceutical composition comprising (S)-methyl-3-[4-(2-hydroxy-3-isopropylamino) propoxy] phenylpropionate or pharmaceutically acceptable salt thereof, wherein the pharmaceutical composition is substantially free of (R)-methyl-3-[4-(2-hydroxy-3-isopropylamino) propoxy] phenylpropionate or a pharmaceutically acceptable salt thereof, and the subject is in need of treatment for tachycardia with control of associated hypotension, wherein a therapeutically equivalent concentration of a pharmaceutical composition comprising (R,S)-methyl-3-[4-(2-hydroxy-3-isopropylamino) propoxy]phenylpropionate hydrochloride is likely to cause the subject to develop hypotension.

2. A method for treating tachycardia in a subject in need thereof, the method comprising:

administering to the subject a therapeutically effective amount of a pharmaceutical composition comprising (S)-methyl-3-[4-(2-hydroxy-3-isopropylamino) propoxy] phenylpropionate or a pharmaceutically acceptable salt thereof, wherein the pharmaceutical composition is substantially free of (R)-methyl-3-[4-(2-hydroxy-3-isopropylamino) propoxy] phenylpropionate or a pharmaceutically acceptable salt thereof, and wherein the therapeutically effective amount is administered at a hypotension controlling amount greater than or equal to 0.3 μmol/kg/min, wherein a therapeutically equivalent concentration of a pharmaceutical composition comprising RS-meth l-3-[4-(2-hydroxy-3-isopropylamino) propoxy] phenylpropionate hydrochloride is likely to cause the subject to develop hypotension.

3. The method of claim 1, wherein the therapeutically effective amount comprises a hypotension controlling amount of (S)-methyl-3-[4-(2-hydroxy-3-isopropylamino) propoxy] phenylpropionate or pharmaceutically acceptable salt thereof.

4. The method of claim 3, wherein the hypotension controlling amount of (S)-methyl-3-[4-(2-hydroxy-3-isopropylamino) propoxy] phenylpropionate or pharmaceutically acceptable salt thereof is greater than or equal to 37.5 nmol/kg/min.

5. The method of claim 1, wherein a dose corresponding to greater than or equal to 25 μg/kg/min of racemic esmolol hydrochloride is indicated.

6. A method for treating tachycardia in a subject, the method comprising:

administering to the subject a therapeutically effective amount of a pharmaceutical composition comprising (S)-methyl-3-[4-(2-hydroxy-3-isopropylamino) propoxy] phenylpropionate or pharmaceutically acceptable salt thereof, wherein the pharmaceutical composition is substantially free of (R)-methyl-3-[4-(2-hydroxy-3-isopropylamino) propoxy] phenylpropionate or a pharmaceutically acceptable salt thereof, and the subject is in need of treatment for tachycardia with control of associated hypotension, wherein the patient has a condition characterized by susceptibility to hypotension.

7. The method of claim 6, wherein the condition characterized by susceptibility to hypotension is selected from the group consisting of aldosterone deficiency, Ulick syndrome, Visser syndrome, Algrove syndrome, tetrahydrobiopterin deficiency, aromatic L-amino acid decarboxylase deficiency, monoamine oxidase deficiency, dopamine-β-hydroxylase deficiency, Biaggioni syndrome, Menkes syndrome, familial dysautonomia, hereditary sensory and motor neuropathies, familial amyloidosis, familial olivopontocerebellar atrophy, mitral valve prolapsed syndrome, hereditary mast cell activation disorder, Bartter syndrome, orthostatic hypotension, familial orthostatic hypotensive disorder, type 1 diabetes, type 2 diabetes, and hypovolemia.

8. The method of claim 1, wherein the patient has a polymorphism in the ADRB2 gene.

9. The method of claim 8 wherein the polymorphism is Gly16Arg (rs1042713; SEQ ID NO: 1).

10. The method of claim 1, wherein the patient is age 65 or older.

11. The method of claim 1, wherein the patient is of Asian ancestry.

12. The method of claim 11, wherein the patient is of Chinese ancestry.

13. The method of claim 1, wherein the patient is undergoing a procedure under spinal anesthesia or was administered spinal anesthesia within the last 36 hours.

14. The method of claim 1, wherein the patient is undergoing a procedure under general anesthesia or was administered general anesthesia within the last 36 hours.

15. The method of claim 1 wherein the pharmaceutical composition contains less than 5% by weight (R)-methyl-3-[4-(2-hydroxy-3-isopropylamino) propoxy] phenylpropionate or a pharmaceutically acceptable salt thereof based on the total amount of methyl-3-[4-(2-hydroxy-3-isopropylamino) propoxy] phenylpropionate or pharmaceutically acceptable salt thereof in the composition.

16. The method of claim 1, wherein the pharmaceutical composition contains less than 2% by weight (R)-methyl-3-[4(2-hydroxy-3-isopropylamino) propoxy] phenylpropionate or a pharmaceutically acceptable salt thereof based on the total amount of methyl-3-[4-(2-hydroxy-3-isopropylamino) propoxy] phenylpropionate or pharmaceutically acceptable salt thereof in the composition.

17. The method of claim 1, wherein the pharmaceutical composition contains less than 0.5% by weight (R)-methyl-3-[4-(2-hydroxy-3-isopropylamino) propoxy] phenylpropionate or a pharmaceutically acceptable salt thereof based on the total amount of methyl-3-[4-(2-hydroxy-3-isopropylamino) propoxy] phenylpropionate or pharmaceutically acceptable salt thereof in the composition.

* * * * *

SEQUENCE LISTING

```
<160> NUMBER OF SEQ ID NOS: 1

<210> SEQ ID NO 1
<211> LENGTH: 52
<212> TYPE: DNA
<213> ORGANISM: Homo sapiens

<400> SEQUENCE: 1
gcagcgcctt cttgctggca cccaatrgaa gccatgcgcc ggaccacgac gt            52
```